(12) United States Patent
Zhu et al.

(10) Patent No.: US 8,187,627 B2
(45) Date of Patent: May 29, 2012

(54) DRESSING DELIVERY SYSTEM FOR INTERNAL WOUNDS

(75) Inventors: Yong Hua Zhu, Redlands, CA (US); Wolff M. Kirsch, Redlands, CA (US)

(73) Assignee: Loma Linda University Medical Center, Loma Linda, CA (US)

( * ) Notice: Subject to any disclaimer, the term of this patent is extended or adjusted under 35 U.S.C. 154(b) by 963 days.

(21) Appl. No.: 10/935,415

(22) Filed: Sep. 7, 2004

(65) Prior Publication Data
US 2005/0095275 A1     May 5, 2005

Related U.S. Application Data

(60) Provisional application No. 60/500,764, filed on Sep. 5, 2003.

(51) Int. Cl.
*A61L 15/00* (2006.01)
*A61F 5/00* (2006.01)
*A61F 13/00* (2006.01)

(52) U.S. Cl. ............... 424/445; 602/41; 602/42; 602/43
(58) Field of Classification Search .................. 424/445; 602/41, 42, 43
See application file for complete search history.

(56) References Cited

U.S. PATENT DOCUMENTS

| | | | |
|---|---|---|---|
| 3,483,870 A | 12/1969 | Coover et al. | |
| 4,166,469 A | 9/1979 | Littleford | |
| 4,394,373 A | 7/1983 | Malette et al. | |
| 4,530,698 A | 7/1985 | Goldstein et al. | |
| 4,531,943 A * | 7/1985 | Van Tassel et al. | 604/523 |
| 4,532,134 A | 7/1985 | Malette et al. | |
| 4,744,363 A | 5/1988 | Hasson | |
| 4,772,266 A | 9/1988 | Groshong | |
| 4,890,612 A | 1/1990 | Kensey | |
| 4,921,479 A | 5/1990 | Grayzel | |
| 4,999,235 A | 3/1991 | Lunn et al. | |
| 5,015,249 A | 5/1991 | Nakao et al. | |
| 5,139,486 A | 8/1992 | Moss | |
| 5,176,128 A | 1/1993 | Andrese | |
| 5,192,301 A | 3/1993 | Kamiya et al. | |
| 5,192,302 A | 3/1993 | Kensey et al. | |
| 5,236,455 A | 8/1993 | Wilk et al. | |
| 5,257,979 A | 11/1993 | Jagpal | |

(Continued)

FOREIGN PATENT DOCUMENTS
CA    2274066    2/2006
(Continued)

OTHER PUBLICATIONS

"Microporous Polysaccharide Hemispheres Provides Effective Topical Hemostasis in a Human Modified Bleeding Time Incision Model" by MEDAFOR, Sep. 2002.*

(Continued)

*Primary Examiner* — Isis Ghali
(74) *Attorney, Agent, or Firm* — Knobbe, Martens, Olson & Bear, LLP

(57) ABSTRACT

A dressing delivery system comprises an applicator for holding and positioning a wound dressing. The applicator comprises a sleeve having a distal spreading portion. The wound dressing is disposed on or adjacent the spreading portion. The applicator urges the dressing into contact with the wound. The sleeve is advanced to actuate the spreading portion, which increases the diameter of the applicator and preferably deploys the dressing.

21 Claims, 18 Drawing Sheets

U.S. PATENT DOCUMENTS

| | | | |
|---|---|---|---|
| 5,259,835 | A | 11/1993 | Clark et al. |
| 5,282,827 | A | 2/1994 | Kensey et al. |
| 5,290,310 | A | 3/1994 | Makower et al. |
| 5,292,311 | A | 3/1994 | Cope |
| 5,292,332 | A | 3/1994 | Lee |
| 5,300,065 | A | 4/1994 | Anderson |
| 5,306,259 | A | 4/1994 | Fischell et al. |
| 5,320,639 | A | 6/1994 | Rudnick |
| 5,360,397 | A | 11/1994 | Pinchuk |
| 5,370,660 | A | 12/1994 | Weinstein et al. |
| 5,383,896 | A | 1/1995 | Gershony et al. |
| 5,383,899 | A | 1/1995 | Hammerslag |
| 5,395,383 | A * | 3/1995 | Adams et al. ................ 606/151 |
| 5,397,311 | A | 3/1995 | Walker et al. |
| 5,405,360 | A | 4/1995 | Tovey |
| 5,419,765 | A | 5/1995 | Weldon et al. |
| 5,431,639 | A | 7/1995 | Shaw |
| 5,437,631 | A | 8/1995 | Janzen |
| 5,445,597 | A | 8/1995 | Clark et al. |
| 5,458,131 | A | 10/1995 | Wilk |
| 5,480,380 | A | 1/1996 | Martin |
| 5,486,195 | A | 1/1996 | Myers et al. |
| 5,529,577 | A | 6/1996 | Hammerslag |
| 5,545,178 | A | 8/1996 | Kensey et al. |
| 5,554,118 | A | 9/1996 | Jang |
| 5,556,375 | A | 9/1996 | Ewall |
| 5,596,990 | A | 1/1997 | Yock et al. |
| 5,620,461 | A | 4/1997 | Muijs Van Moer et al. |
| 5,632,727 | A | 5/1997 | Tipton et al. |
| 5,643,318 | A | 7/1997 | Tsukernik et al. |
| 5,645,566 | A | 7/1997 | Brenneman et al. |
| 5,649,959 | A | 7/1997 | Hannam et al. |
| 5,653,730 | A | 8/1997 | Hammerslag |
| 5,662,681 | A | 9/1997 | Nash et al. |
| 5,665,106 | A | 9/1997 | Hammerslag |
| 5,665,107 | A | 9/1997 | Hammerslag |
| 5,676,689 | A | 10/1997 | Kensey et al. |
| 5,684,042 | A | 11/1997 | Greff et al. |
| 5,725,551 | A | 3/1998 | Myers et al. |
| 5,728,132 | A | 3/1998 | Van Tassel et al. |
| 5,759,169 | A | 6/1998 | Marx |
| 5,759,194 | A | 6/1998 | Hammerslag |
| 5,776,096 | A | 7/1998 | Fields |
| 5,810,810 | A | 9/1998 | Tay et al. |
| 5,811,091 | A | 9/1998 | Greff et al. |
| 5,836,970 | A * | 11/1998 | Pandit ........................... 606/213 |
| 5,843,124 | A | 12/1998 | Hammerslag |
| 5,906,631 | A | 5/1999 | Imran |
| 5,910,155 | A | 6/1999 | Ratcliff et al. |
| 5,928,266 | A | 7/1999 | Kontos |
| 5,971,956 | A | 10/1999 | Epstein |
| 6,004,341 | A | 12/1999 | Zhu et al. |
| 6,007,563 | A | 12/1999 | Nash et al. |
| 6,048,358 | A | 4/2000 | Barak |
| 6,056,768 | A | 5/2000 | Cates et al. |
| 6,155,265 | A | 12/2000 | Hammerslag et al. |
| 6,159,178 | A | 12/2000 | Sharkawy et al. |
| 6,198,016 | B1 | 3/2001 | Lucast et al. |
| 6,287,322 | B1 | 9/2001 | Zhu et al. |
| 6,287,323 | B1 | 9/2001 | Hammerslag |
| 6,315,753 | B1 | 11/2001 | Cragg et al. |
| 6,371,974 | B1 | 4/2002 | Brenneman |
| 6,425,901 | B1 | 7/2002 | Zhu et al. |
| 6,461,364 | B1 | 10/2002 | Ginn et al. |
| 6,508,828 | B1 | 1/2003 | Akerfeldt et al. |
| 6,524,326 | B1 | 2/2003 | Zhu et al. |
| 2003/01/0982 | | 6/2003 | Gross et al. |
| 6,589,269 | B2 | 7/2003 | Zhu et al. |
| 6,613,070 | B2 | 9/2003 | Redmond et al. |
| 6,649,162 | B1 | 11/2003 | Biering et al. |
| 6,890,342 | B2 | 5/2005 | Zhu et al. |
| 6,964,675 | B2 | 11/2005 | Zhu et al. |
| 2001/0004710 | A1 | 6/2001 | Felt et al. |
| 2001/1001859 | | 8/2001 | Cruise et al. |
| 2002/0077656 | A1 | 6/2002 | Ginn et al. |
| 2002/0111647 | A1 * | 8/2002 | Khairkhahan et al. ........ 606/200 |
| 2002/0147479 | A1 | 10/2002 | Aldrich |
| 2003/0023267 | A1 | 1/2003 | Ginn |
| 2003/0050590 | A1 | 3/2003 | Kirsch |
| 2003/0050665 | A1 | 3/2003 | Ginn |
| 2003/0158578 | A1 | 8/2003 | Pantages et al. |
| 2004/0054346 | A1 | 3/2004 | Zhu et al. |
| 2004/0059348 | A1 | 3/2004 | Geske et al. |
| 2005/0107826 | A1 | 5/2005 | Zhu et al. |
| 2005/0118238 | A1 | 6/2005 | Zhu et al. |
| 2005/0123588 | A1 | 6/2005 | Zhu et al. |
| 2005/0142172 | A1 | 6/2005 | Kirsch et al. |
| 2005/0209637 | A1 | 9/2005 | Zhu et al. |
| 2005/0240137 | A1 | 10/2005 | Zhu et al. |
| 2006/0064124 | A1 | 3/2006 | Zhu et al. |
| 2007/0123816 | A1 | 5/2007 | Zhu et al. |

FOREIGN PATENT DOCUMENTS

| | | |
|---|---|---|
| CA | 2334226 | 4/2006 |
| EP | 0 028 452 A1 | 5/1981 |
| EP | 0 482 350 A2 | 4/1992 |
| EP | 0 745 350 A1 | 12/1996 |
| EP | 0 955 900 | 7/2005 |
| FR | 2574285 A1 | 6/1986 |
| WO | WO 94 21306 A1 | 9/1994 |
| WO | WO 95/05206 | 2/1995 |
| WO | WO 96 10374 A1 | 4/1996 |
| WO | WO 96 24291 | 8/1996 |
| WO | WO 97 20505 A1 | 6/1997 |
| WO | WO 98 24374 A1 | 6/1998 |
| WO | WO 99 22646 A1 | 5/1999 |
| WO | WO 99 42535 A1 | 8/1999 |
| WO | WO 99 62405 A1 | 12/1999 |
| WO | WO 00 02488 A1 | 1/2000 |
| WO | WO 00 07640 A2 | 2/2000 |
| WO | WO 00 19912 A1 | 4/2000 |
| WO | WO 00 33744 A1 | 6/2000 |
| WO | WO 01 62159 A2 | 8/2001 |
| WO | WO 02/05865 A2 | 1/2002 |
| WO | WO 02/09591 A2 | 2/2002 |
| WO | WO 03 008002 A2 | 1/2003 |
| WO | WO 03 008003 A1 | 1/2003 |
| WO | WO 03 105697 | 12/2003 |
| WO | WO 2004/110284 A1 | 12/2004 |

OTHER PUBLICATIONS

Angio-Seal, Hemostasis Puncture Closure Device Brochure, Sherwood Medical Co., Jun. 11, 1997.

Medafor, Inc. Adds Two management Team Members, Press Release, Jun. 7, 2001, http://www.medafor.com/new0601.html.

* cited by examiner

DRESSING DELIVERY SYSTEM FOR INTERNAL WOUNDS

RELATED APPLICATIONS

This application is based on and claims priority to U.S. Provisional Application No. 60/500,764, which was filed on Sep. 5, 2003. The entirety of the priority application is hereby incorporated by reference.

BACKGROUND OF THE INVENTION

1. Field of the Invention

This invention relates to a wound closure device, and more specifically to a device and method for applying a dressing onto a wound during a surgical procedure.

2. Description of the Related Art

In an effort to minimize patient trauma, many types of surgeries are typically performed through as small of an incision as possible. Such minimally invasive surgical procedures can be used to treat various types of internal wounds. These wounds can be, for example, surgical incisions, accident-caused injuries, bleeding tumors or ulcers, tumor beds from which a tumor has been surgically removed, or any other tissue area requiring treatment. However, closure of internal wounds using minimally invasive procedures may be problematic and difficult. If blood flow from such a subcutaneous wound cannot be effectively and confidently arrested, the clinician must convert from laparoscopic or endoscopic surgery to open surgery in order to gain sufficient access to the tissue to enable closure of the wound through traditional open-surgery techniques such as suturing or clips.

Endoscopic surgery typically involves a cannula or trocar inserted through a relatively small incision through the patient's outer tissue layers to provide access to the patient's internal organs. Access to the surgical field during endoscopic surgery is limited. Thus, a limitation of endoscopic surgery is that it is relatively difficult to use multiple tools to effect wound closure. As a result, surgical instruments may be called upon to perform tasks without the aid of other instruments. However, consistent and reliable closure of a wound using only a single instrument is difficult to achieve. Further, surgical tools must fit through a narrow trocar of cannula.

SUMMARY OF THE INVENTION

Accordingly, there is a need in the art for a single surgical instrument that can access internal wounds through a confined space, and apply a suitable dressing to the wound.

In accordance with one embodiment, a wound closure device is provided. The device can be a dressing applicator having an elongate body with inner and outer lumens. First and second connectors provide access to the inner and outer lumens, respectively. The lumens each have distal openings and the inner lumen distal opening is distal of the outer lumen distal opening. In some embodiments, the inner and outer lumens are arranged concentrically.

In one embodiment, a vacuum source may be removably connected to one of the first and second connectors. The vacuum source is preferably configured to releasably hold a dressing disposed at the distal opening of the lumen of said connector while the closure device is advanced to the wound location to deploy the dressing. The dressing can be deployed by pressing the dressing onto the wound location with the applicator. Further, a distal portion of the applicator preferably spreads the dressing onto the wound. In another embodiment, an adhesive source may be removably connected to another of the first and second connectors, wherein the adhesive source is configured to deliver a flowable adhesive over and around the dressing once the dressing is deployed over the wound.

In another embodiment, a dressing applicator comprises a sleeve having a body and a lumen extending about an axis between a proximal end and a distal end. The distal end of the body defines at least one foldable portion configured to pivot between an orientation generally parallel to the axis of the lumen and an orientation generally orthogonal to the axis. For example, the at least one foldable portion can pivot about a junction in the body wall, such as a hinge.

In one embodiment, the distal end of the body is configured to releasably hold the dressing while the sleeve is advanced to the wound location or field area. Once the dressing is at the wound location, the at least one foldable portion may be pivoted into an orientation generally transverse to the axis, and preferably generally parallel to the dressing and wound location. In one embodiment, a clinician using the applicator may continue to advance the sleeve toward the wound location, causing the at least one foldable portion to pivot upon coming in contact with the wound.

In another embodiment, a locking or actuation mechanism is configured to hold the at least one foldable portion generally parallel to the axis. The locking mechanism can be actuated to allow the at least one foldable portion to pivot into an orientation generally transverse to the axis. The at least one foldable portion can then be used to compress and/or hold the dressing against the wound and/or the field area surrounding the wound. Optionally, a flowable adhesive may be delivered over and around the dressing, as described above. In one embodiment, the flowable adhesive can be delivered via at least one aperture formed on the body of the dressing applicator.

In still another embodiment, the dressing may be disposed circumferentially about the at least one foldable portion of the sleeve. The dressing thus extends about the axis as the sleeve is advanced to the wound location or field area. In one embodiment, the sleeve can have apertures formed at a distal end thereof for applying a vacuum therethrough to hold the dressing on the sleeve. Once the distal end of the sleeve is proximal the wound location, the at least one foldable portion is pivoted, as discussed above, to push the dressing onto the wound. The at least one foldable portion can then be used to compress and/or hold the dressing against the field area surrounding the wound.

In one embodiment, the sleeve having foldable portions can define a lumen configured to slidably receive an elongate body of a dressing applicator therein. The applicator is configured to removably hold a dressing generally orthogonal to an axis of the applicator, as the applicator and dressing are advanced to the wound location. In one embodiment, a vacuum source, as discussed above, can be used to hold the dressing. In another embodiment, the dressing is held by an adhesive. Once the dressing is positioned at the wound location, the sleeve can be advanced about the body toward the dressing. In one embodiment, the foldable portions of the sleeve can pivot upon contacting the dressing to expand the diametrical cross section of the applicator and to compress and/or hold the dressing on the wound. In another embodiment, the foldable portions can pivot upon contacting a catch at the distal end of the applicator body.

In another embodiment, the elongate body of a dressing applicator, as described above, can have foldable portions at a distal end of the applicator. Upon deployment of the dressing over the wound location, the foldable portions can be pivoted generally orthogonal to an axis of said body, via for example contact with the wound location, to compress and/or hold the dressing over the wound location.

DETAILED DESCRIPTION OF THE PREFERRED EMBODIMENTS

Figure 1:
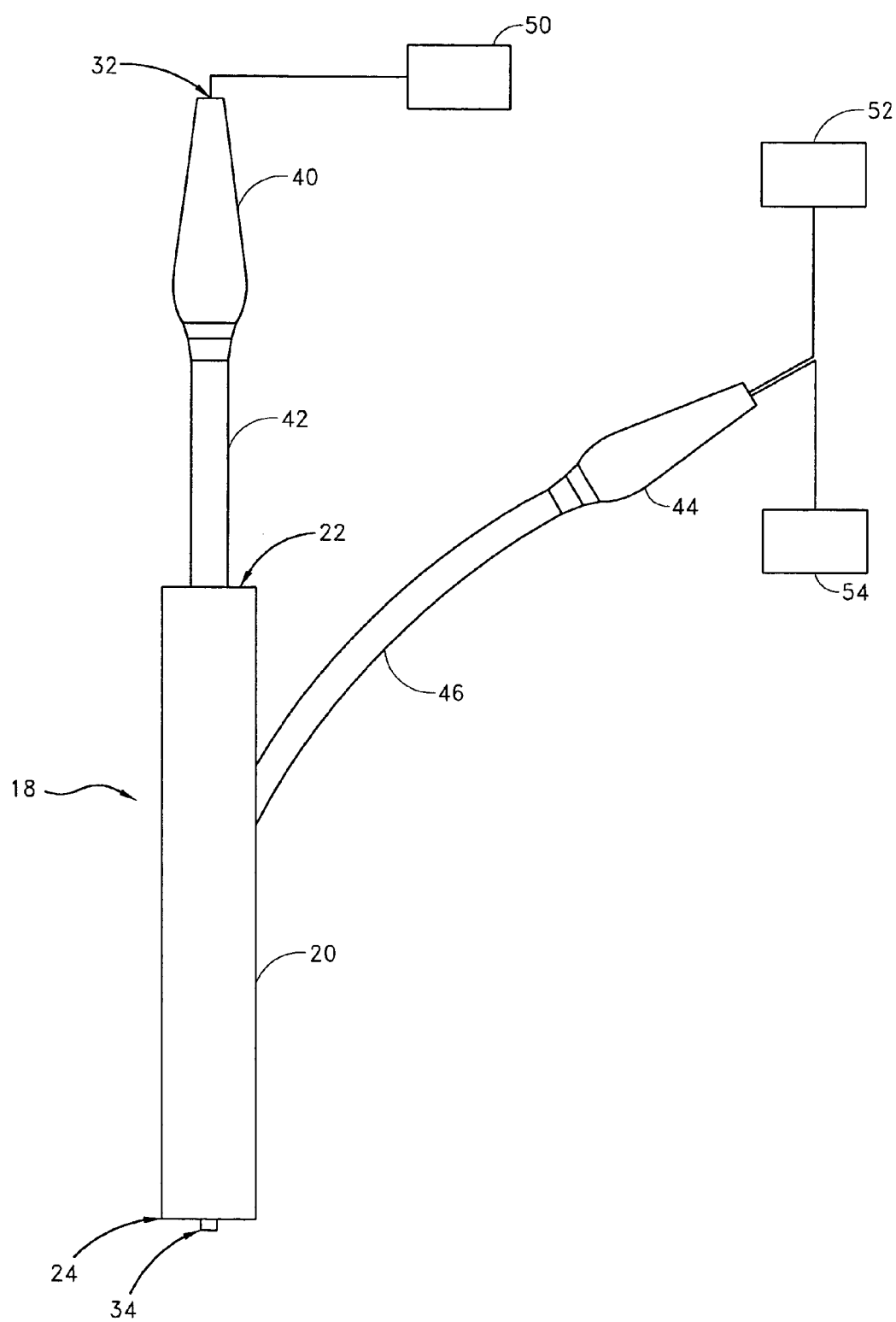
FIG. 1 is a side view of one embodiment of a dressing applicator.

FIG. 1 shows a side view of one embodiment of a dressing applicator 18. The applicator 18 preferably comprises a tubular main body 20 having a generally cylindrical wall 20a (see FIG. 2) extending between a proximal end 22 and a distal end 24. The cylindrical wall 20a defines a lumen 26 therein that extends between the proximal end 22 and a distal opening 28 at the distal end 24 of the tubular main body 20. The applicator 18 also preferably comprises a tubular inner body 30 having a generally cylindrical inner wall 30a that extends between a proximal end 32 and a distal end 34. The inner wall 30a defines a lumen 36 extending between the proximal end 32 and a distal opening 38 at the distal end 34 of the tubular inner body 30. In the illustrated embodiment, the tubular main body 20 and the tubular inner body 30 are concentric about a major axis Y. It is to be understood that other configurations may desirably be employed.

Figure 2:
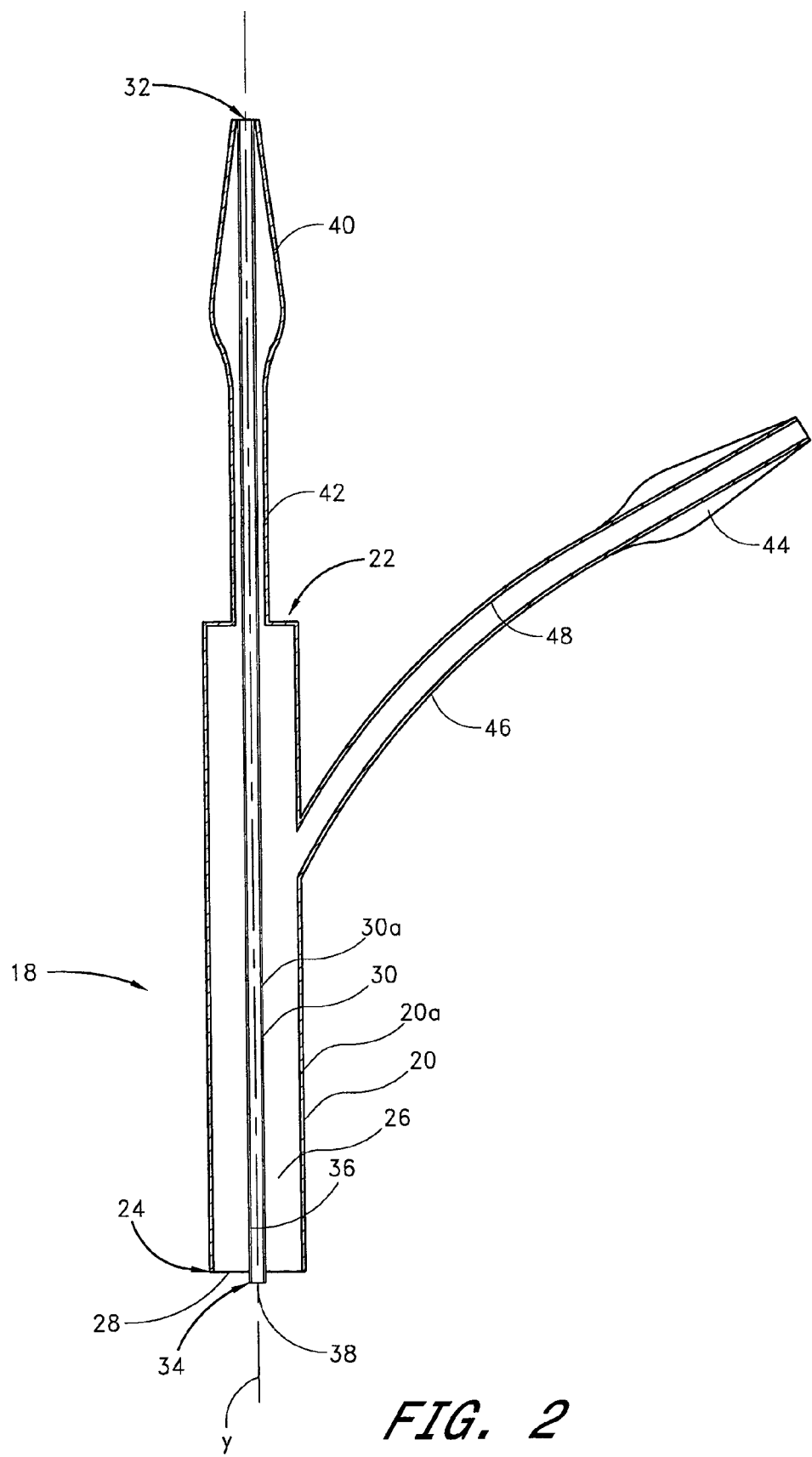
FIG. 2 is a cross-sectional view of the dressing applicator of FIG. 1.

As shown in FIGS. 1 and 2, a first connector 40 is connected to the proximal end 22 of the tubular main body 20 via a first neck 42. Additionally, a second connector 44 is connected to the cylindrical wall 20a of the tubular main body 20 via a second neck 46. As shown in FIG. 2, the inner lumen 36 can extend through the first neck 42 and the first connector 40 to the proximal end 32 of the lumen 36. Additionally, another lumen 48 may extend from the main body 20 through the second neck 46 and the second connector 44. The lumen 48 preferably communicates with the outer lumen 26.

Each of the connectors 40, 44 preferably is adapted to be selectively connected to a variety of medical devices. For example, in one embodiment one of the connectors 40, 44 can be connected to a vacuum source 50 (shown schematically). In another embodiment, one of the connectors 40, 44 can be removably connected to a fluid source 52 (not shown) that supplies a fluid such as an irrigation liquid, a hemostatic agent, medication, or the like. In still another embodiment, one of the connectors 40, 44 can be removably connected to a source of flowable adhesive 54 (shown schematically). Further details concerning some embodiments of a dressing applicator can be found in Applicants' U.S. Pat. No. 6,589, 269, the entirety of which is hereby incorporated by reference.

Figure 3:
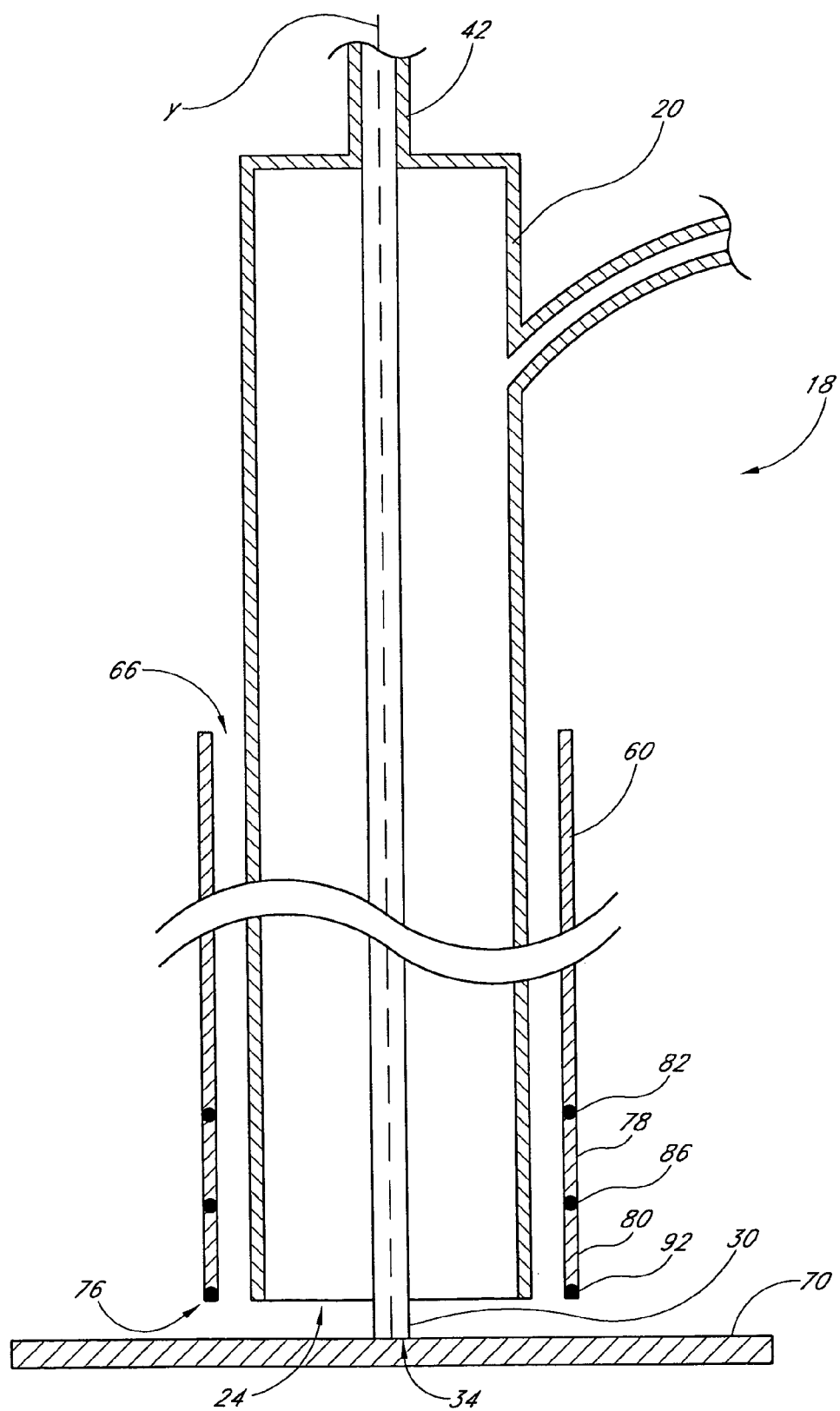
FIG. 3 is a sectional side view of a dressing applicator according to another embodiment, the applicator having a sleeve with a spreading portion.
Figure 4:
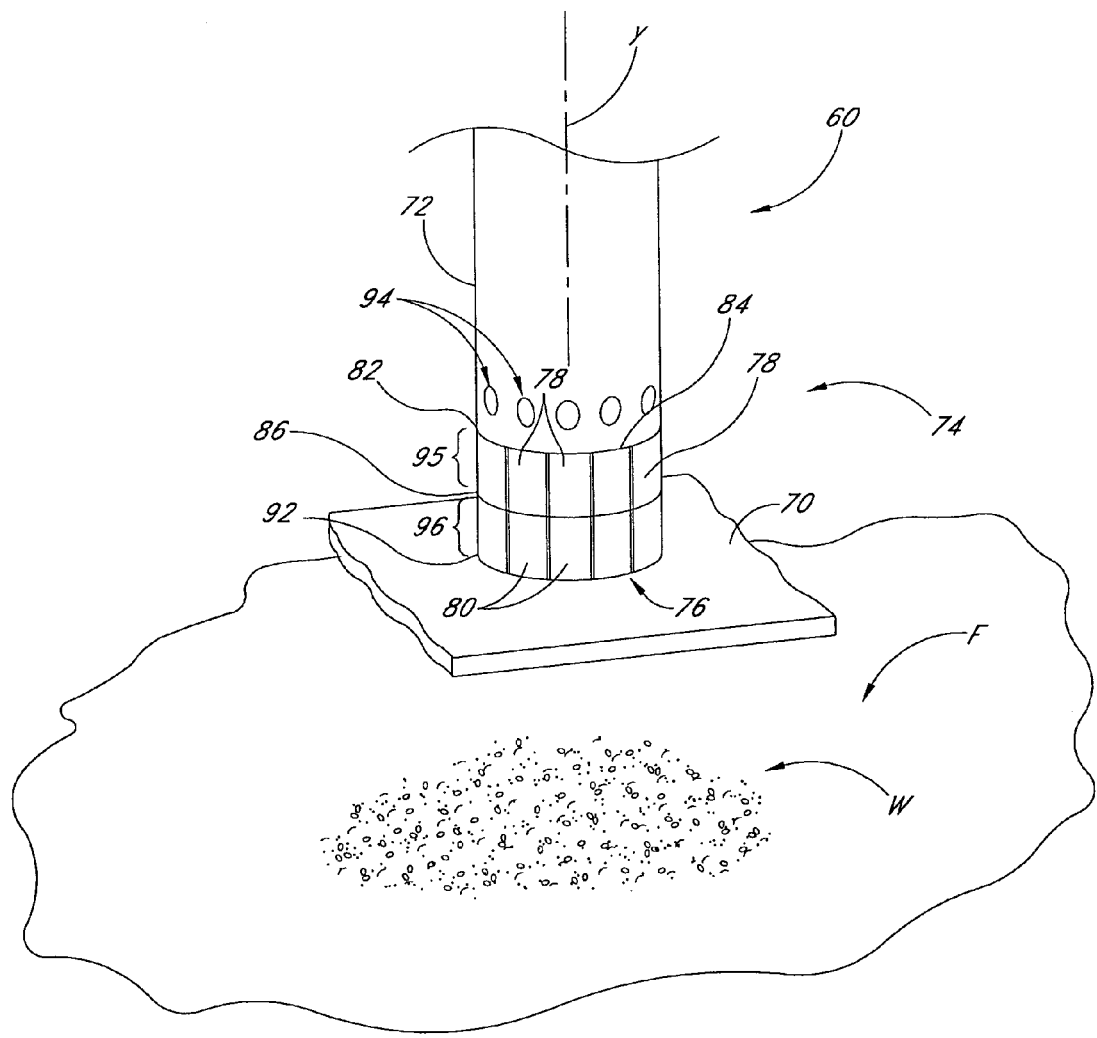
FIG. 4 is a partial perspective view of the dressing applicator of FIG. 3 with the spreading portion in an unfolded state.

With reference next to FIGS. 3-4, another embodiment of a dressing applicator 18 additionally comprises a tubular sleeve 60 having a wall 60a that defines a lumen 66. The lumen 66 is configured to sidably receive the tubular main body 20 of the applicator 18 therethrough. The tubular inner body 30 removably holds a dressing 70 at its distal end 34 via, for example, a vacuum pulled through the inner lumen 36.

Figure 5:
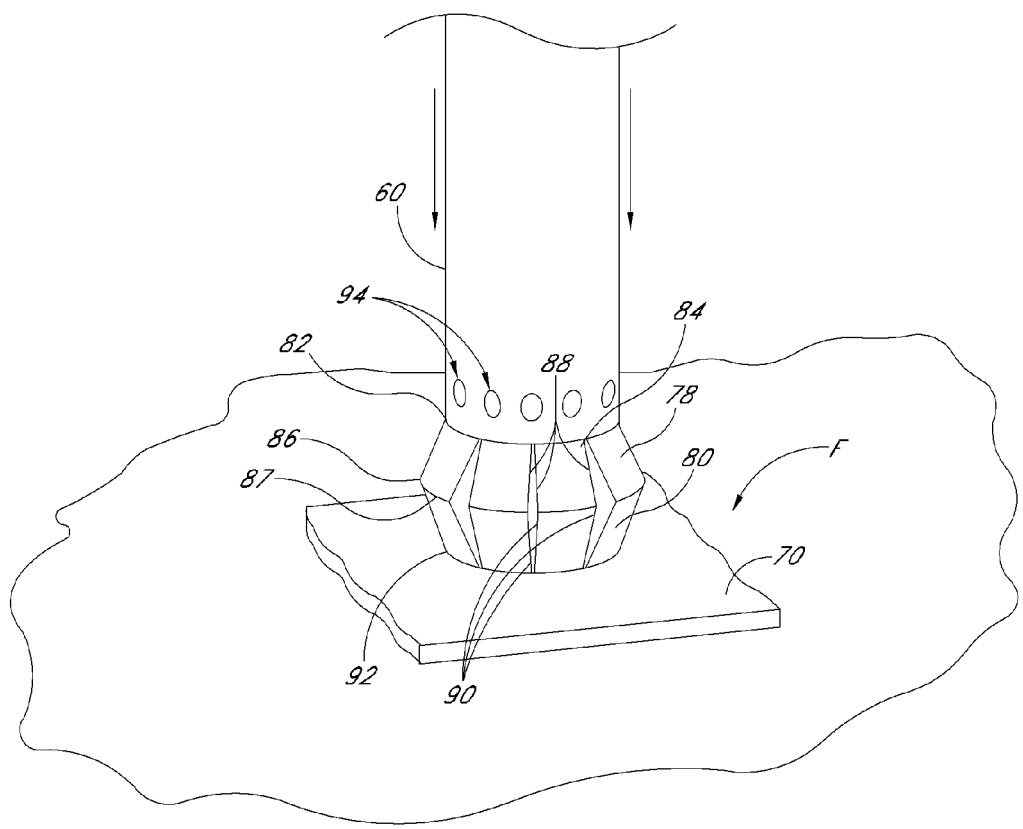
FIG. 5 is a partial perspective view of the dressing applicator of FIG. 3 with the spreading portion in an intermediate state.
Figure 6:
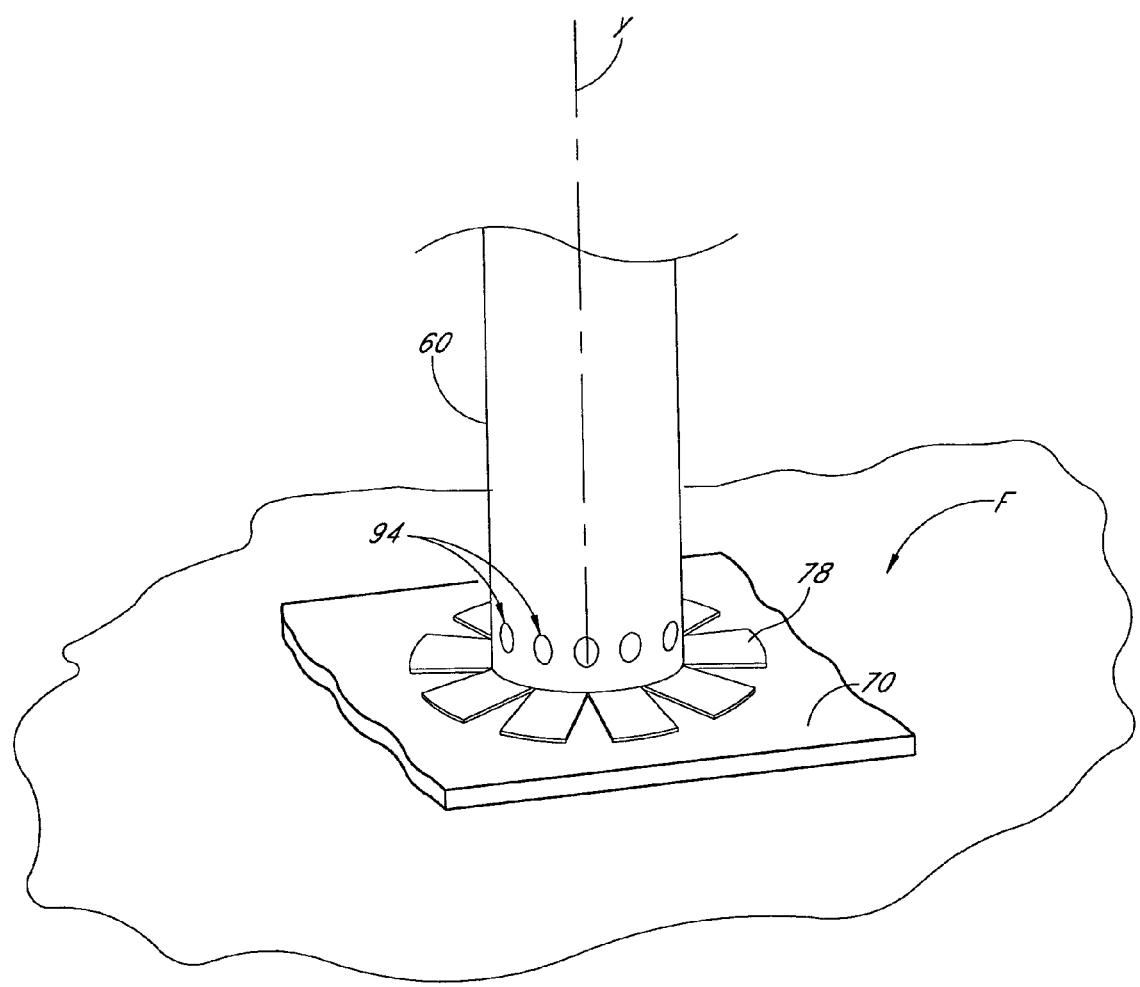
FIG. 6 is a partial perspective view of the dressing applicator of FIG. 3 with the spreading portion in a fully deployed state.

The tubular sleeve 60 preferably comprises a generally rigid portion 72 and at least one spreading portion 74 disposed between the rigid portion 72 and a distal end 76 of the sleeve 60. In the illustrated embodiment the tubular sleeve 60 comprises a plurality of upper segments 78 each connected to the generally rigid portion 72, and a corresponding plurality of lower segments 80 connected to respective upper segments 80 and extending to the distal end 76 of the sleeve 60. With reference also to FIGS. 5 and 6, the segments 78, 80 are preferably configured to moveably pivot between an orientation generally parallel to the major axis Y and an orientation generally orthogonal to the axis Y.

Each upper segment 78 pivotably connects to the generally rigid portion 72 via a proximal joint 82 so as to define a pivoting edge 84 between the upper segment 78 and the generally rigid portion 72. In one embodiment, the proximal joint 82 allows the upper segment 78 to pivot in a direction away from the major axis Y. Preferably, the proximal joint 82 comprises a hinge. It is to be understood that the proximal joint 82 can include any structure allowing the upper segments 78 to pivot relative to the major axis Y. For example, in one embodiment the proximal joint 82 can be a scored section extending about the circumference of the sleeve 60, where the scored section is preferentially bendable to allow the upper segments 78 to pivot relative to the rigid portion 72. In another embodiment, the proximal joint 82 can be a circumferential section of the sleeve wall 60a having a reduced thickness, where the section of reduced thickness is preferentially bendable to allow the upper segments 78 to pivot relative to the rigid portion 72.

With continued reference to FIGS. 3-6, each lower segment 80 preferably is pivotally connected to the respective upper segment 78 via an intermediate joint 86 so as to define a pivoting edge 87 between the upper segment 78 and the lower segment 80. In one embodiment, the intermediate joint 86 can allow the lower segment 80 to pivot away from the major axis Y. As with the proximal joint 82, the intermediate joint 86 can comprise any structure configured to allow the lower segments 80 to pivot relative to the major axis Y and the upper segments 78, such as a hinge, scored section, or section of reduced thickness.

Each of the upper segments 78 comprises side edges 88 extending from the proximal joint 82 to the intermediate joint 86. Similarly each of the lower segments 80 comprises side edges 90 that extend from the intermediate joint 86 to a distal joint 92. In the illustrated embodiment, the side edges 88 of adjacent upper segments 78 generally engage each other when the segments are oriented generally parallel to the major axis Y, as shown in FIG. 4. Similarly the side edges 90 of the adjacent lower segments 80 generally engage each other when the segments are oriented generally parallel to the major axis Y. Accordingly there is generally no gap between the segments when in this position. It is to be understood that, in other embodiments, the segments can be arranged so that there are gaps between the side edges 88, 90 of adjacent segments 78, 80 when the segments are oriented generally parallel to the major axis Y.

Each lower segment 80 preferably is pivotally connected to a distal joint 92 at or adjacent to the distal end 76 of the sleeve 60. The lower segment 80 pivots at the distal joint 92. As with the proximal and intermediate joints 82, 86, the distal joint 92 can comprise any structure configured to allow the lower segment 80 to pivot relative to the major axis Y. With particular reference to FIG. 5, preferably the lower segments 80 are configured so that each distal joint 92 generally maintains its radial distance from the major axis Y, and the distal joints 92 of successive segments 80 are immediately adjacent another. Preferably, the distal joints 92 are linked so as not to separate them from one another.

FIGS. 4-6 illustrate an embodiment of a dressing applicator 18 having a tubular sleeve 60 in operation deploying a dressing 70 upon a wound W. The wound W depicted in FIG. 3 simulates a tumor bed from which a tumor has been surgically removed. Such a wound W tends to ooze and bleed slowly over a relatively large area. If the oozing is not controlled, open surgery techniques may be required to properly dress the wound W and arrest the bleeding. Of course, one of ordinary skill in the art will understand that other types of wounds are also amenable to the embodiments disclosed herein, such as wounds to internal organs and vasculature.

FIG. 4 shows the sleeve 60 in an unfolded position, in which the segments 78, 80 are generally aligned with the major axis Y. FIG. 5 shows the sleeve 60 in a partially folded orientation in which the segments 78, 80 are positioned generally transverse to the major axis Y. FIG. 6 shows the sleeve 60 in a completely folded orientation in which the segments 78, 80 are positioned generally orthogonal, or generally perpendicular, to the major axis Y.

With continued reference to FIGS. 3-6, in one embodiment the dressing 70 is applied to the distal end 34 of the inner body 30 and a vacuum is drawn therethrough in order to hold the dressing 70 in place. The device is then advanced toward the wound W as shown in FIG. 4. After the device has been advanced so that the dressing 70 has contacted the wound W, the clinician preferably applies a force to the sleeve 60 so as to advance the sleeve distally relative to the main tubular body 20. The generally rigid portion 72 of the sleeve 60 preferably is sufficiently rigid to push distally without buckling. The distal end 76 of the sleeve 60 contacts the wound W through the dressing 70. Upon continued application of force, the upper and lower segments 78, 80 buckle or pivot about the joints 82, 86, 92, as shown in FIG. 5. The upper segment 78 pivots outward relative to the major axis Y so that its outer surface faces generally away from a surgical field F surrounding the wound W. The lower segment 80 pivots outwardly relative to the major axis Y so that its outer surface generally faces toward the field F. As the segments 78, 80 pivot, the edge 84 between the upper and lower segments 78, 80 displaces radially outwardly from the major axis Y.

As the sleeve 60 continues to move distally relative to the main body 20, the segments 78, 80 continue to fold and the pivoting edge 84 continues to move radially outwardly from the major axis Y. Eventually, as shown in FIG. 6, the segments 78, 80 are substantially completely folded. The lower segments 80 are in contact with the dressing, and a compression force from the sleeve 60 is translated through the segments 80 to the dressing 70. As such, in the fully deployed state, the effective circumference of the applicator is increased, and compression force urging the dressing 70 against the wound W is distributed across a larger area than is provided when the dressing applicator 18 is in a non-folded arrangement. A more secure placement of the dressing 70 on the wound W is thus achieved. Additionally, in some embodiments, the present device and method can be used to compress the dressing 70 against the field F surround the wound W as well as the wound itself. After the dressing 70 is suitably deployed and spread, the sleeve 60 may be moved proximally to return the segments 78, 80 to the unfolded state.

In the embodiment shown in FIGS. 3-6, at least one aperture 94 preferably is formed on the generally rigid portion 72 of the sleeve 60 and communicates with the lumen 66 of the sleeve 60. The at least one aperture 94 is configured to allow, for example, a flowable adhesive therethrough onto and about the dressing 70. Other substances, such as a medication, hemostatic agent, irrigation fluid, or the like can also or alternatively be supplied through the at least one aperture 94 to the field F around a wound W.

In the illustrated embodiment, a length 95 of the upper segments 78 is substantially equal to a length 96 of the lower segments 80. In other embodiments, the lengths can be different. For example, in another embodiment, the length 95 of the upper segments 78 is greater than the length 96 of the lower segments 80. As such, when the lower segments 80 are deployed generally perpendicular to the sleeve 60, the upper segments 78 are still somewhat angled, and efficiently communicate compression force to the intermediate joint 86 and throughout the lower segments 80. Still further, in such an embodiment the lower segments 80 can be deployed and angled beyond an angle perpendicular to the sleeve 60, and thus may be used in applications involving convex wound application surfaces.

With reference next to FIGS. 7-10, another embodiment of an applicator 98 comprises a main body 20 having a distal end 24 and comprising a tubular sleeve 60 that is slidable relative to the main body 20. In the illustrated embodiment, the main body defines a lumen 26, and the distal end 24 of the main body 20 comprises a distal wall 100. Preferably, the distal wall 100 is substantially solid. In other embodiments, the distal wall may include at least one aperture, and may comprise a mesh, netting, or the like. Preferably, the sleeve 60 is similar to the sleeve discussed above in connection with FIGS. 3-6.

Figure 7:
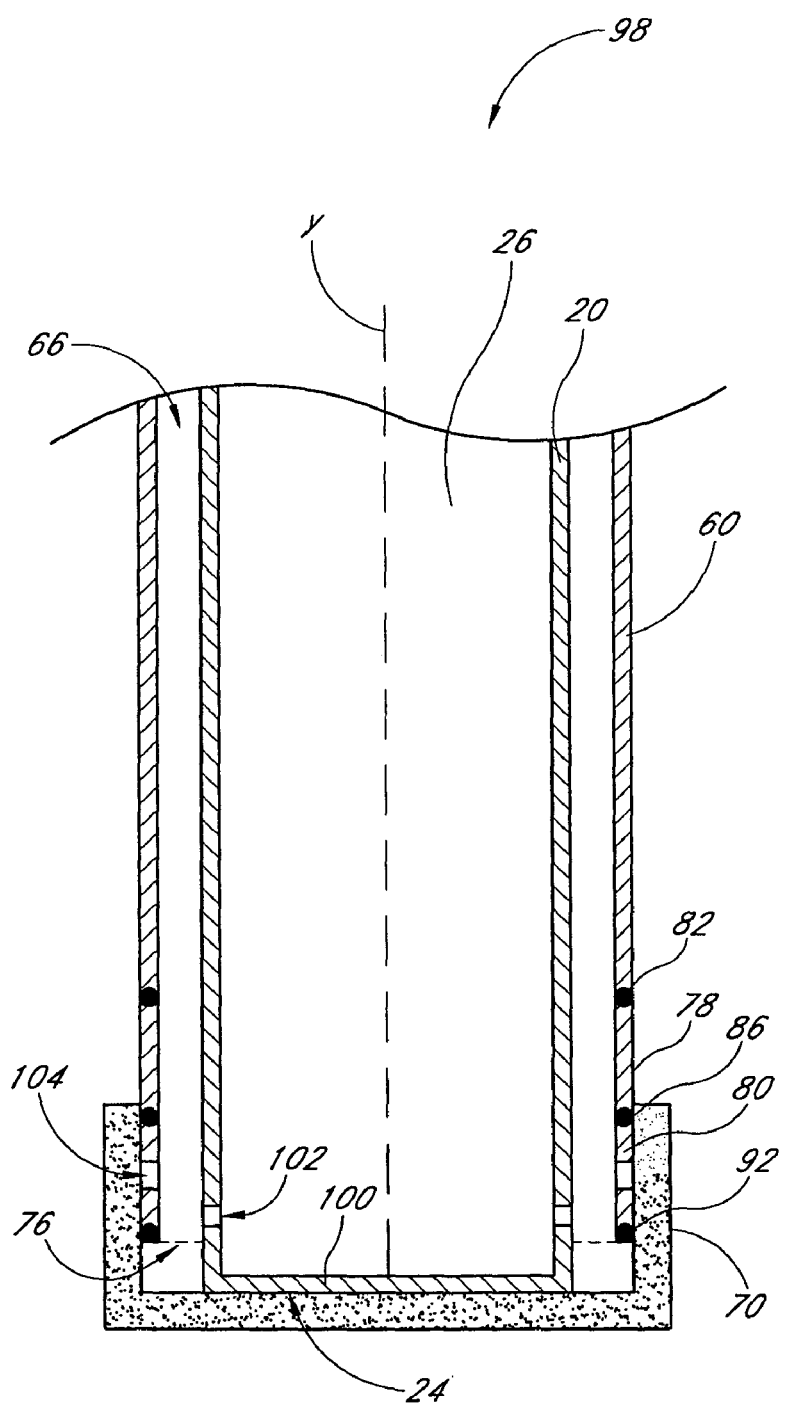
FIG. 7 is a cross-sectional partial side view of another embodiment of a dressing applicator, wherein the dressing is removably held about a distal end of a sleeve.
Figure 8:
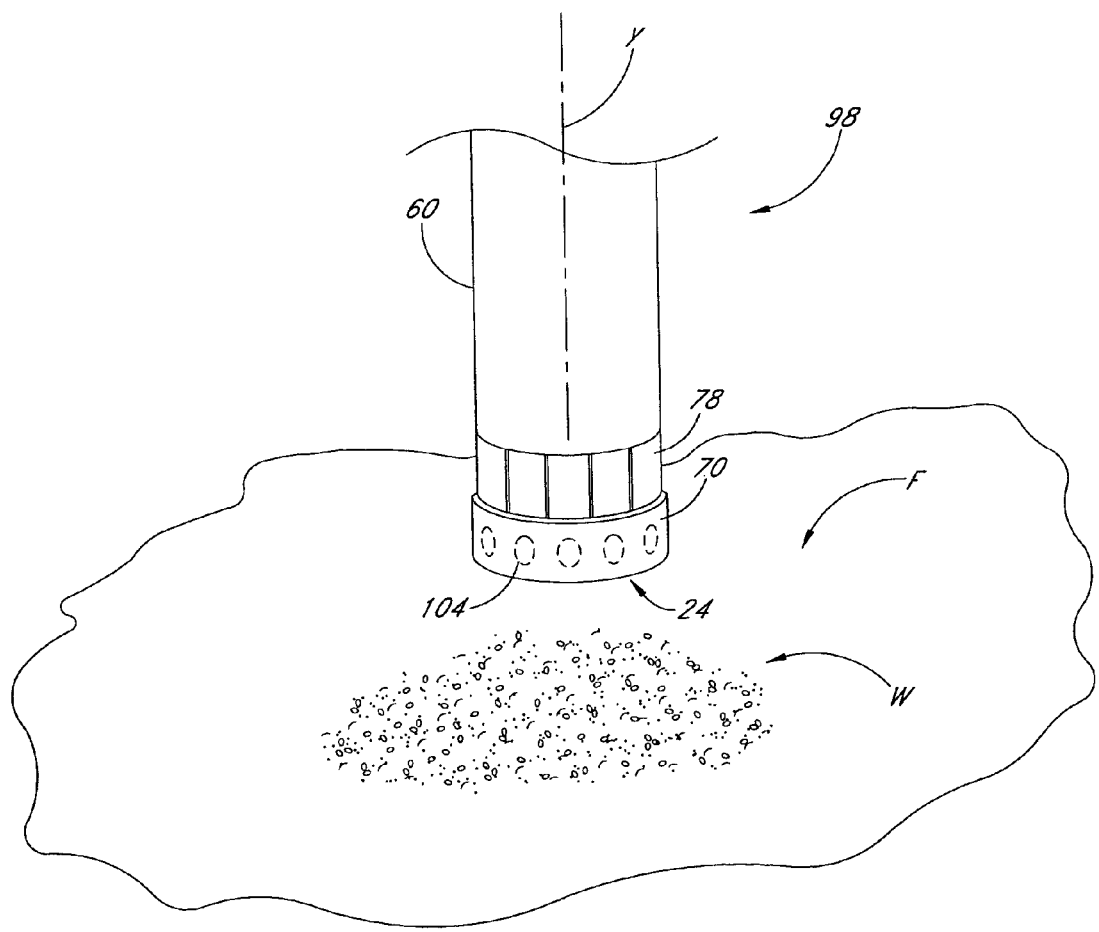
FIG. 8 is a partial perspective view of the arrangement of FIG. 7 with the spreading portion in an unfolded state.
Figure 9:
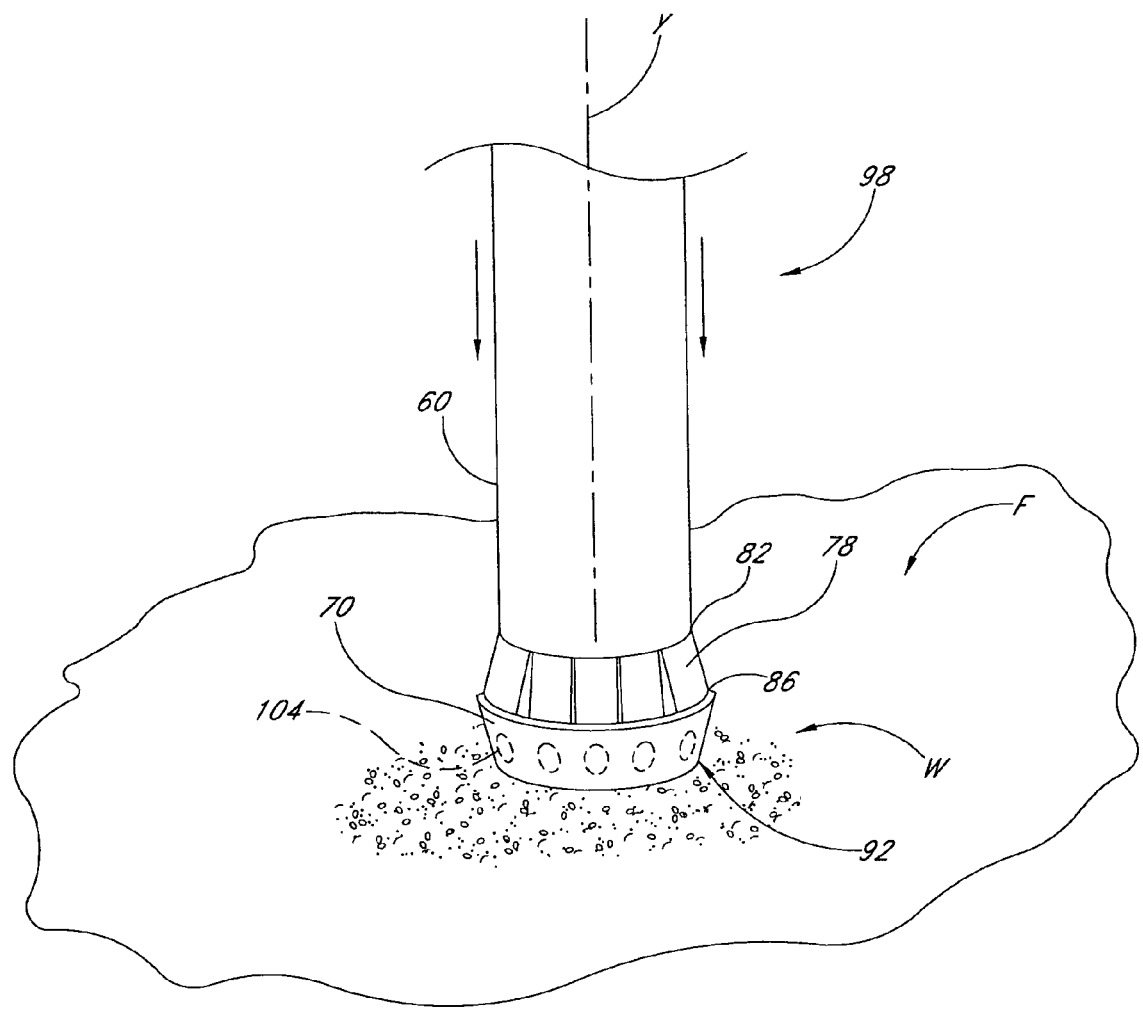
FIG. 9 is a partial perspective view of the arrangement of FIG. 7 with the spreading portion in an intermediate state.
Figure 10:
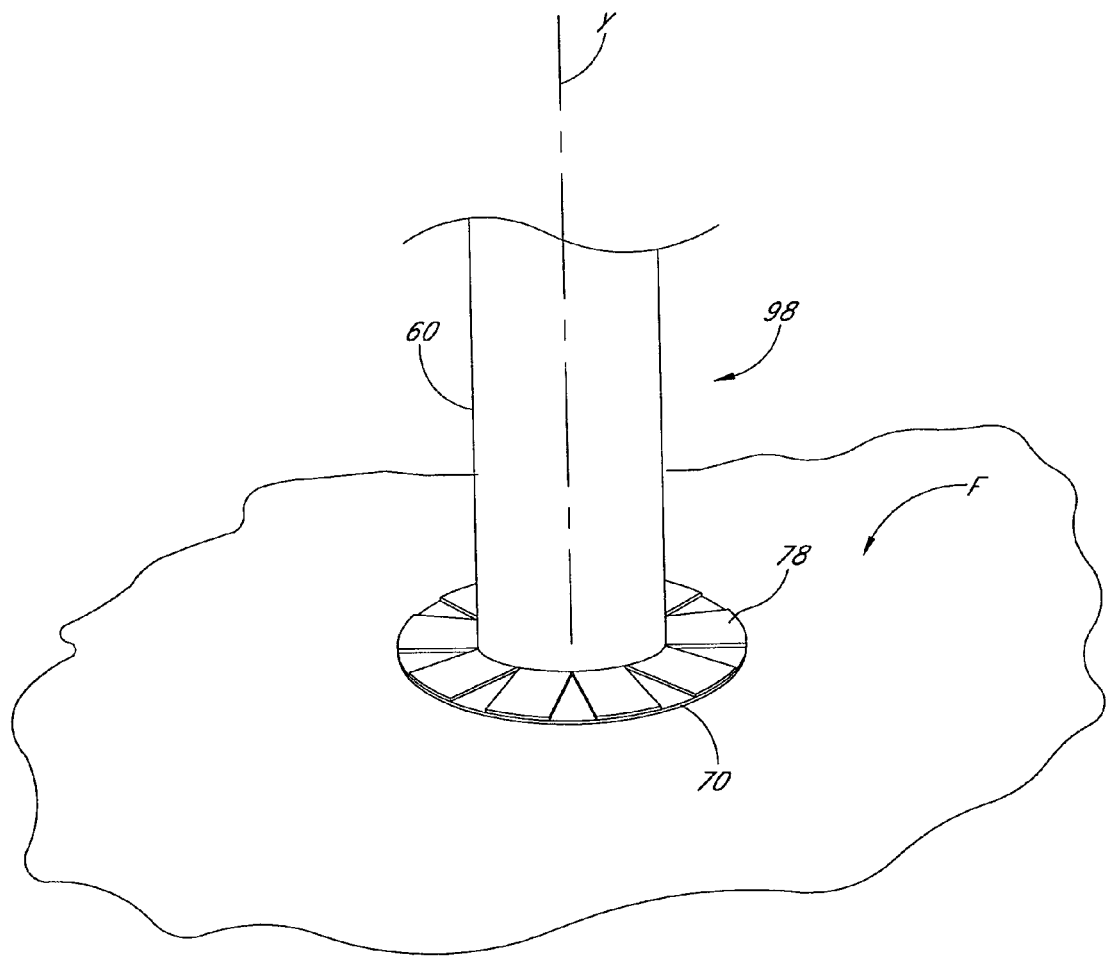
FIG. 10 is a partial perspective view of the arrangement of FIG. 7 with the spreading portion in a fully deployed state.

With particular reference to FIG. 7, the main body 20 preferably comprises one or more apertures 102 formed through a side wall 20a. One or more of the lower segments 80 of the sleeve 60 additionally comprises an aperture 104. Preferably, the sleeve 60 has a lumen 66 that is configured to maintain a vacuum so that a vacuum drawn through the main body lumen 26 further draws a vacuum through the apertures 102, 104.

As shown in FIG. 7, the dressing 70 preferably is disposed circumferentially about the distal ends 24, 76 of the main body 20 and sleeve 60, and is at least partially wrapped thereabout so as to be about at least portions of the lower segments 80. As such, the vacuum through the apertures 104 holds the dressing 70 in place on the distal end of the device 98 in a generally compact arrangement before and while the device 98 is introduced into the patient.

With continued reference to FIGS. 7-10, in operation, a clinician preferably inserts the applicator 98 through a minimally invasive incision and advances the dressing 70 toward the field F of the wound W. Once the distal end 24 of the body 20 contacts the wound W, the clinician moves the sleeve 60 distally relative the body 20 so as to pivot the segments 78, 80 into a fully or partially deployed state. As the segments 78, 80 pivot into a deployed state, the dressing 70 is unwrapped from the sleeve 60 and deployed onto the wound W. The lower segments 80 communicate pressure to urge the dressing 70 securely onto the wound W.

In a preferred embodiment, the vacuum being pulled through the at least one aperture 104 is terminated prior to deploying the dressing 70. Thus, the dressing is more easily is removed from the sleeve 60. In another embodiment, the vacuum is not terminated; however, as the upper and lower segments 78, 80 fold, gaps between the side edges 88, 90 of the segments defeat the vacuum so that the dressing 70 is no longer held securely onto the segments 80 by the vacuum. In another embodiment, the vacuum is also drawn through an aperture or series of openings through the distal wall 100 of the main body 20.

In still another embodiment, instead of or in addition to using a vacuum, the dressing 70 is removably attached to the lower segments 80 via a light adhesive such that the dressing 70 can be detached from the lower segments 80 via the application of a mild force, such as by twisting the applicator once the dressing is deployed. In yet another embodiment, the dressing 70 is removably attached to the lower segments 80 by mechanical means such as, for example, a plurality of hooks or the like. The dressing 70 can be detached from the lower segments 80 by unhooking said hooks via, for example, the application of a rotational force to the sleeve 60.

The dressing 70 can comprise any material suitable for treatment of internal wounds, such as incisions, or oozing tissues, such as ulcers, tumors, or tumor beds from which tumors have been surgically removed. In one embodiment, the dressing 70 comprises a fibrous or sponge-like material infused with a hemostatic agent configured to arrest the flow of blood from the wound W. The dressing 70 can also be made of, for example, PTFE, biovascular material, collagen, Gore-Tex®, Dacron™, etc. The dressing is preferably made of materials that will dissolve over time within the patient's body. Further, the dressing is also preferably hydrophilic so that the dressing 70 will readily adhere to the wound W.

In a particularly preferred embodiment, the dressing comprises a woven or non-woven fabric comprising a hemostatic agent. The hemostatic agent preferably comprises a starch such as bioabsorbable microporous polysaccharide microspheres (e.g., TRAUMADEX™ marketed by Emergency Medical Products, Inc. of Waukesha, Wis.). The microspheres have micro-replicated porous channels. The pore size of the microspheres facilitates water absorption and hyperconcentration of albumin, coagulation factors, and other protein and cellular components of the blood. The microspheres also affect platelet function and enhance fibrin formulation. In addition, the microspheres are believed to accelerate the coagulation enzymatic reaction rate. When applied directly, with pressure, to an actively bleeding wound, the particles act as molecular sieves to extract fluids from the blood. The controlled porosity of the particle excludes platelets, red blood cells, and serum proteins larger than 25,000 Daltons, which are then concentrated on the surface of the particles. This molecular exclusion property creates a high concentration of platelets, thrombin, fibrinogen, and other proteins on the particle surface, producing a gelling action. The gelled, compacted cells and constituents accelerate the normal clotting cascade. The gelling process initiates within seconds, and the resulting clot, while exceptionally tenacious, breaks down normally along with the microparticles. Such microporous polysaccharide microspheres, and additional hemostatic agents, are discussed in more detail in Applicants' copending application entitled "Deployable Multifunctional Hemostatic Agent," U.S. application Ser. No. 10/868,201, filed Jun. 14, 2004, the entirety of which is hereby incorporated by reference.

Any suitable hemostatic substrate can be employed as a support for the hemostatic agents of preferred embodiments. However, in a particularly preferred embodiment the hemostatic substrate comprises chitosan. Chitosan is obtained from chitin, a biopolymer obtained principally from shrimp and crab shell waste. Chitosan is the main derivative of chitin, and is the collective term applied to deacetylated chitins in various stages of deacetylation and depolymerization. Chitosan exhibits anti-inflammatory and analgesic effects, and promotes hemostasis and wound healing. Chitosan has also been used as a hemostatic agent in surgical treatment and wound protection. The hemostatic effect of chitosan has been described in U.S. Pat. No. 4,394,373.

A single hemostatic substrate or combination of hemostatic substrates of different forms and/or compositions can be employed in the devices of preferred embodiments. Different substrate forms can be preferred, for example, fibrous puff, fleece, woven or non-woven fabric, sheet, suture, or powder. A homogeneous mixture of different substrate-forming materials can be employed, or composite substrates can be prepared from two or more different formed substrates. Additional details concerning chitosan and other suitable substrates are discussed in more detail in Applicants' copending application "Deployable Multifunctional Hemostatic Agent."

The applicators 18, 98 illustrated and discussed in connection with FIGS. 1-9 can be made of any biocompatible material suitable for use in surgical procedures for treating subcutaneous wounds. Preferably, the applicator 18, 98 is made of a sterilized and hypoallergenic material. For example, the applicator can be made of a sterilized metal, such as stainless steel or aluminum. In other embodiments, the applicator can be made of a sterilized plastic, such as polyurethane or polypropylene.

Figure 11:
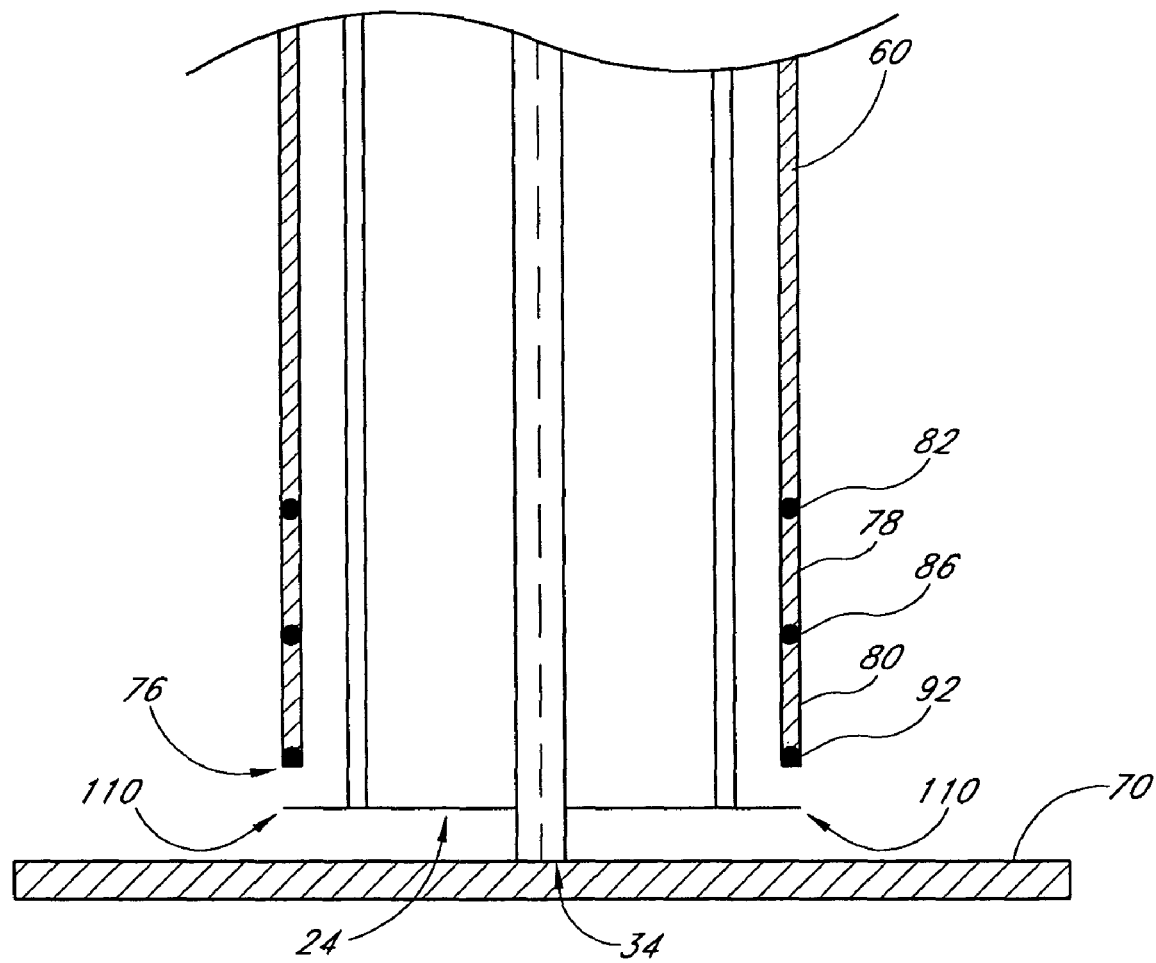
FIG. 11 is a longitudinal cross-section of another embodiment of a dressing applicator having a catch for operatively contacting a sleeve.

In another embodiment, shown in FIG. 11, a catch 110 is disposed at the distal end 24 of the tubular main body 20. In the illustrated embodiment, the catch 110 comprises a lip extending radially outward from the body 20. The catch 110 is configured to contact and limit the translation of the distal end 76 of the sleeve 60 as the sleeve is advanced over the tubular main body 20 and toward the wound. The distal end 76 of the sleeve 60 will contact the catch 110 as the clinician applies force to the sleeve 60 to advance the sleeve to the wound. Once the distal end 76 is in contact with the catch 110, continued application of said force will cause the segments 78, 80 to buckle or pivot relative to the major axis Y into an orientation generally transverse to the axis Y. The segments 78, 80 are thus deployed to compress and/or hold the dressing 70 on the wound without necessitating the distal end 76 of the sleeve 60 contacting with the wound.

Figure 12:
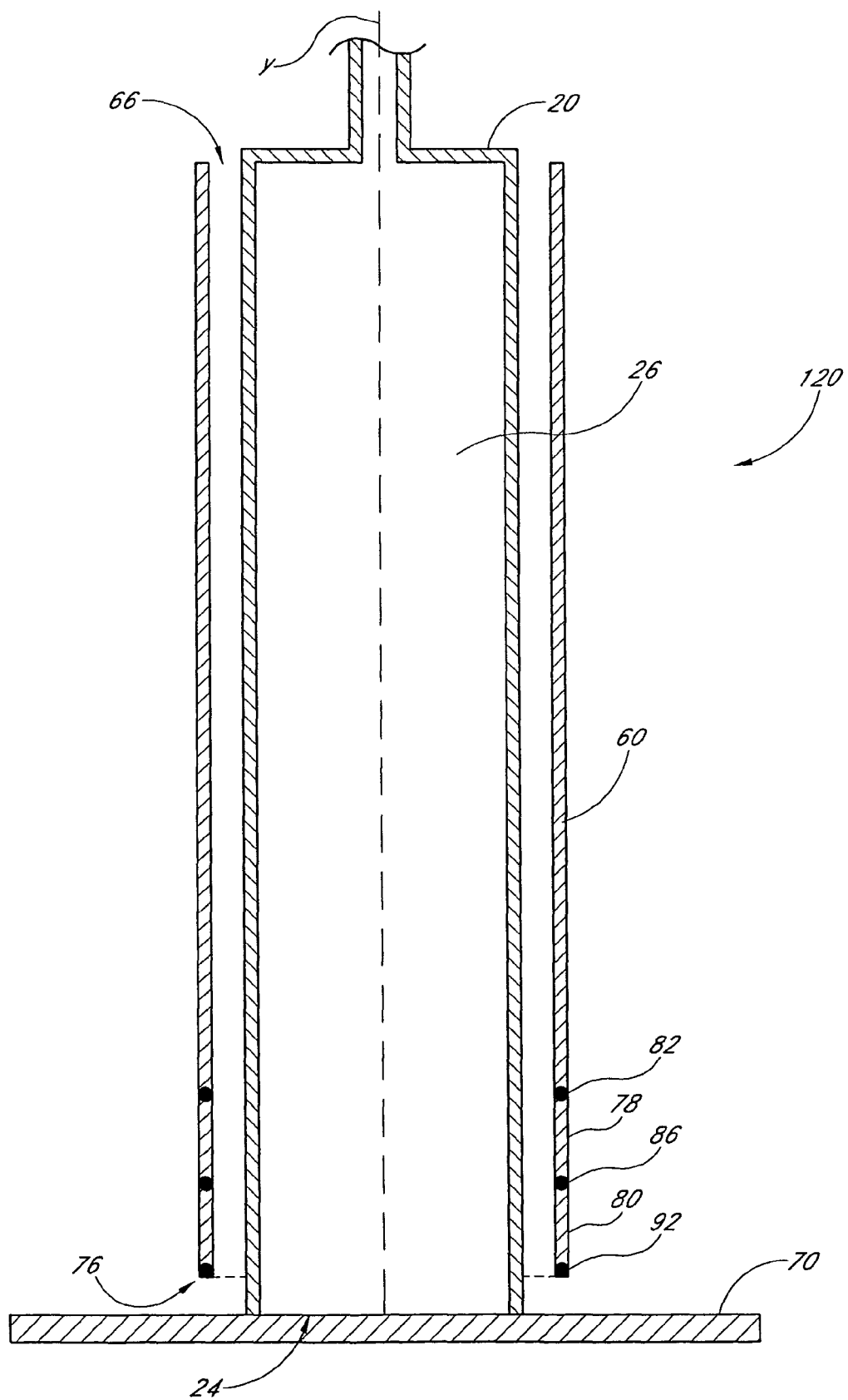
FIG. 12 is a cross-sectional view of another embodiment of a dressing applicator having a dressing removably held at a distal end of a tubular main body.

With reference next to FIG. 12, another embodiment of an applicator 120 comprises a main body 20 having a distal end 24 and comprising a tubular sleeve 60 that is slidable relative to the main body 20. In the illustrated embodiment, the main body defines a lumen 26, and the distal end 24 of the main body 20 comprises a distal opening. Preferably, a vacuum is drawn through the lumen 26, and the vacuum through the distal opening releasably holds a dressing 70 onto the distal end 24. In operation, a clinician advances the body 20 to the wound to dispose the dressing 70 on the wound W. Once the dressing 70 is disposed on the wound, the vacuum is terminated to detach the dressing 70 from the distal end 24 of the body 20. The sleeve 60 is advanced toward the wound to operatively contact the wound W and deploy the dressing 70 thereon.

Figure 13:
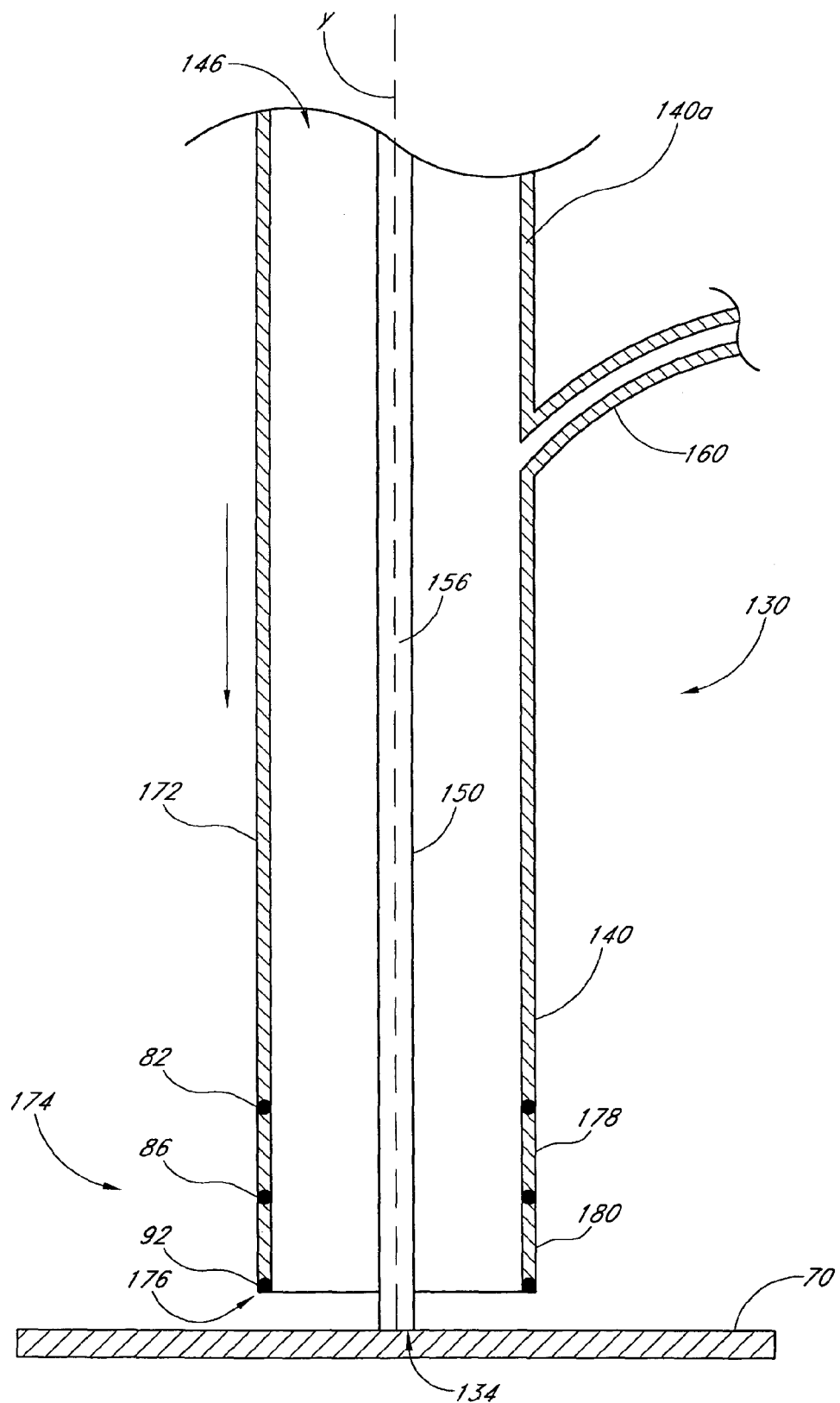
FIG. 13 is a cross-sectional view of another embodiment of a dressing applicator, having a tubular main body movable relative to a tubular inner body.

FIG. 13 shows yet another embodiment of an applicator 130. In the illustrated embodiment, the applicator 130 comprises a tubular main body 140 having a generally cylindrical wall 140a that defines a lumen 146 therein. The applicator 130 also preferably comprises a tubular inner body 150 having a generally cylindrical inner wall that defines a lumen 156 extending between a proximal end and a distal opening 158 at a distal end 154 of the tubular inner body 150. A connector is connected to the cylindrical wall 140a of the tubular main body 140 via a neck 160. Both the inner lumen 156 and outer lumen 146 can be connected to a source of vacuum, fluid or the like.

The tubular main body 140 preferably comprises a generally rigid portion 172 and at least one spreading portion 174 disposed between the rigid portion 172 and a distal end 176 of the body 140. In the illustrated embodiment, the spreading portion 174 comprises a plurality of upper segments 178 and a corresponding plurality of lower segments 180. The respective upper and lower segments 178, 180 preferably are pivotable relative to the rigid portion 172 and each other.

With continued reference to FIG. 13, the tubular main body 140 preferably is movable relative to the tubular inner body 150. As shown, a dressing 70 preferably is removably held at the distal end 154 of the inner body 150 via, for example, a vacuum pulled through the inner lumen 156. In use, the applicator 130 is advanced to a wound so as to position the dressing 70 adjacent the wound W. The main body 140 is then advanced relative to the inner body 150 so that its distal end operatively contacts the wound. Once in contact with the wound W, further application of the force causes the segments 178, 180 to pivot relative to the major axis Y so as to deploy the dressing 70 from the applicator 130 to the wound.

Figure 14:
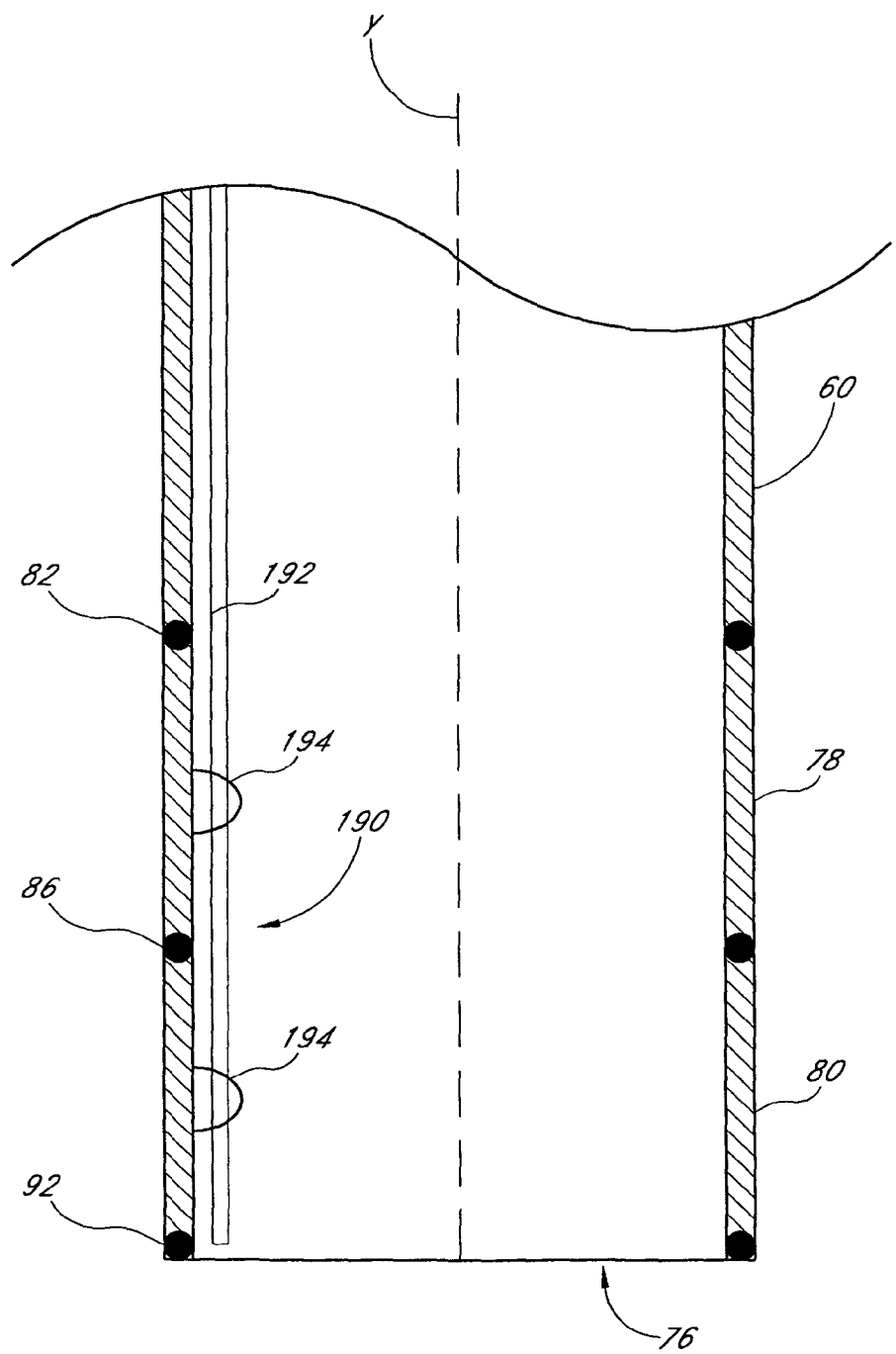
FIG. 14 is a cross-sectional view of a sleeve having a locking mechanism.

In accordance with another embodiment, a locking mechanism can be used to maintain the segments 78, 80 generally parallel to the major axis Y. In the embodiment illustrated in FIG. 14, the proximal and intermediate joints 82, 86 are maintained in a locked position via a locking mechanism 190 when the segments 78, 80 are in an unfolded state. The locking mechanism 190 comprises a rod 192 within the sleeve 60 and extending generally parallel to the axis Y. The rod 192 is configured to slidably extend through at least one locking member 194 connected to the segments 78, 80. In the illustrated embodiment, the at least one locking member 194 consists of two loops. However, the at least one locking member 194 can have other shapes, such as a hook. In a locked position, the rod 192 extends through the at least one locking member 194 to substantially prevent the segments 78, 80 from pivoting relative to the axis Y. To unlock the mechanism 190, the rod 192 is withdrawn from the at least one locking member 194, allowing the segments 78, 80 to pivot relative to the axis Y.

Figure 15:
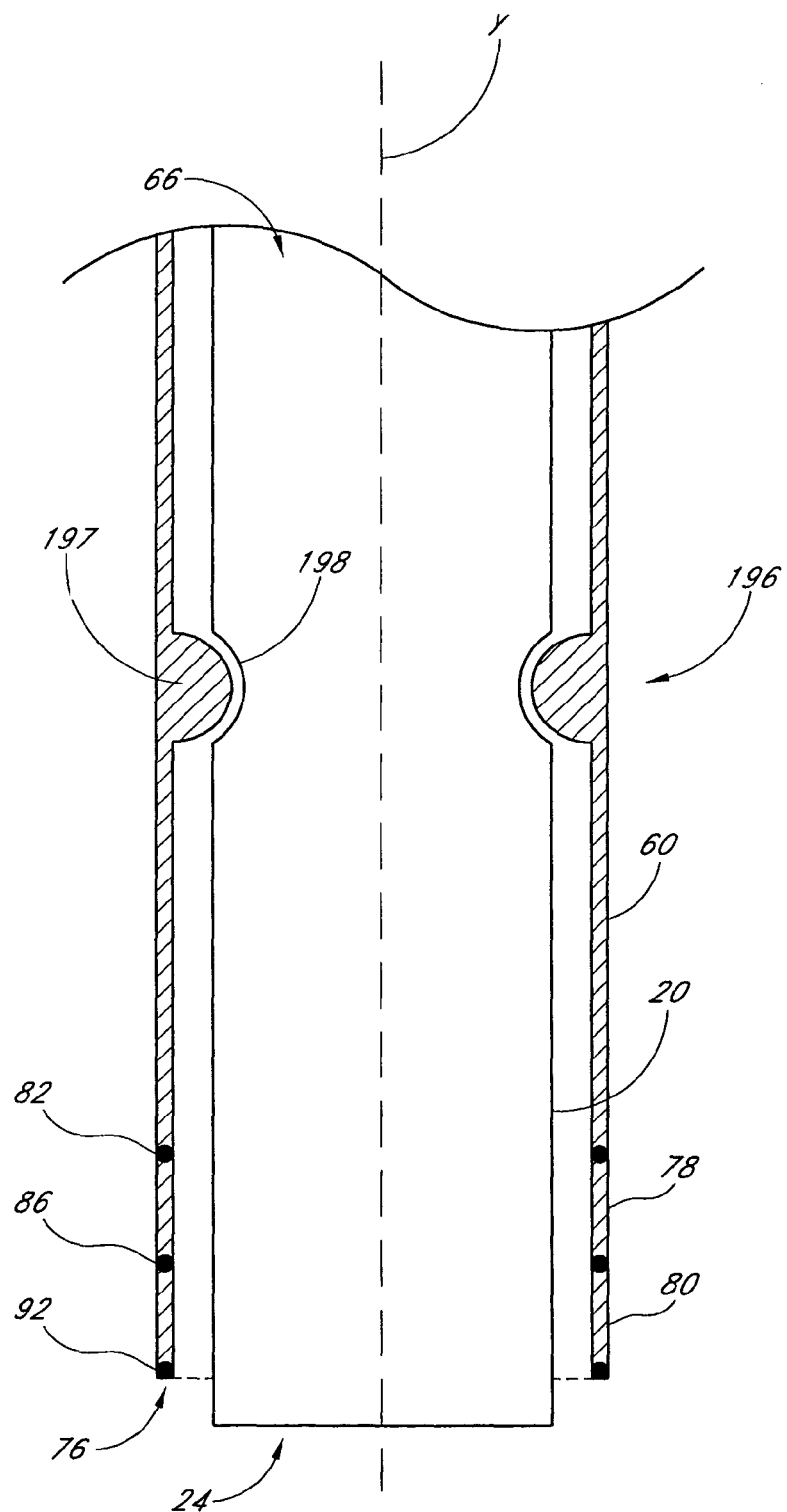
FIG. 15 is a cross-sectional view of another embodiment of a dressing applicator, having a locking mechanism configured to lock a sleeve longitudinally relative to a tubular main body.

In another embodiment, shown in FIG. 15, a locking mechanism 196 configured to lock a sleeve 60 relative to a tubular main body 20 includes at least one protrusion 197 formed on an inner wall of the sleeve 60 and contacting the body 20. The at least one protrusion 197 is preferably configured to operatively engage a corresponding receiving portion 198 formed in or on the tubular main body 20. In the illustrated embodiment, the protrusion 197 and receiving portion 198 comprise a ball and detent. When the protrusion 197 is disposed in the receiving portion 198, the locking mechanism 196 substantially prevents movement of the sleeve 60 relative to the body 20. However, the protrusion 197 disengages from the receiving portion 198 upon application of a releasing force. Once disengaged, the sleeve 60 is free to move relative to the tubular main body 20. In another embodiment, the sleeve and body are partially threaded onto one another.

Figure 16:
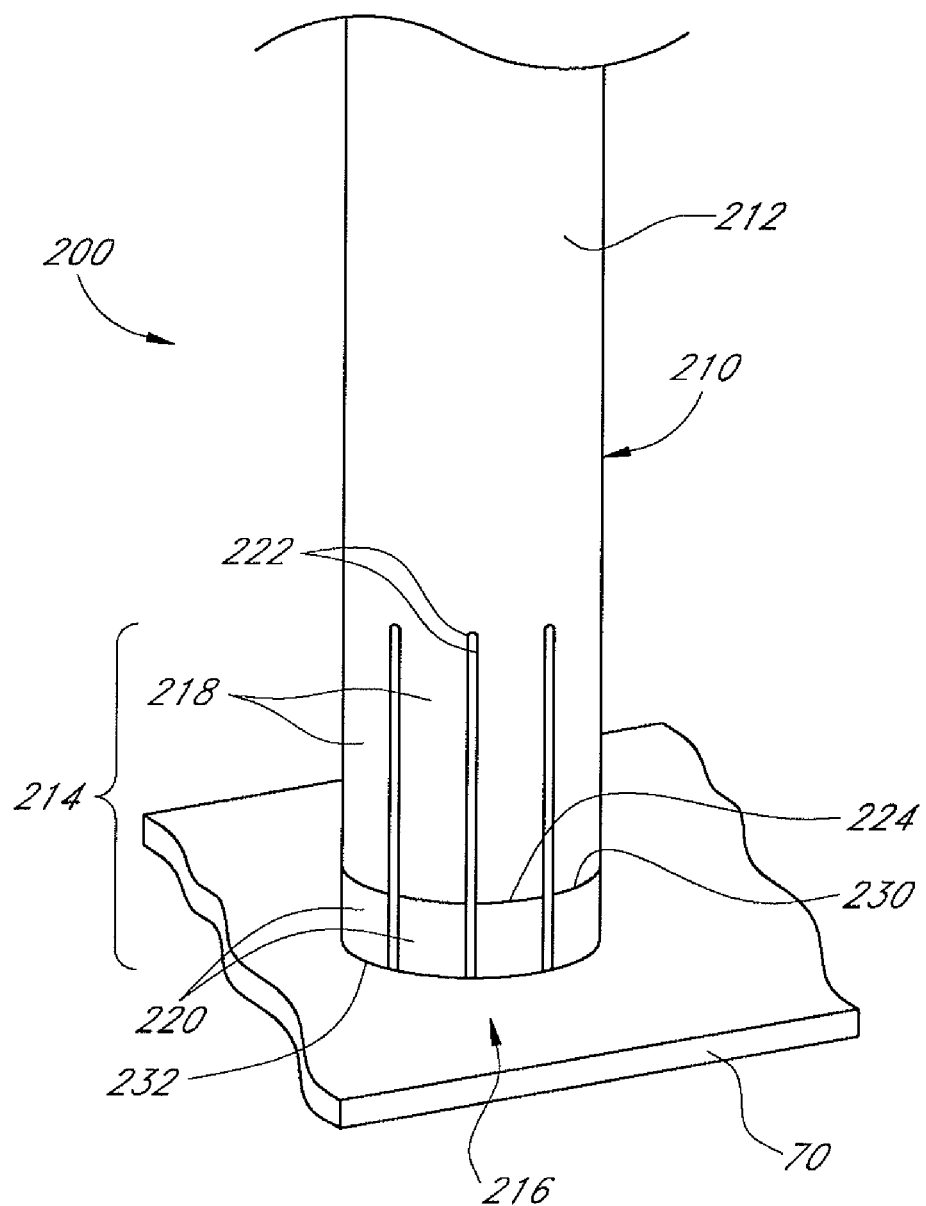
FIG. 16 is a partial perspective view of another embodiment of a dressing applicator.
Figure 17:
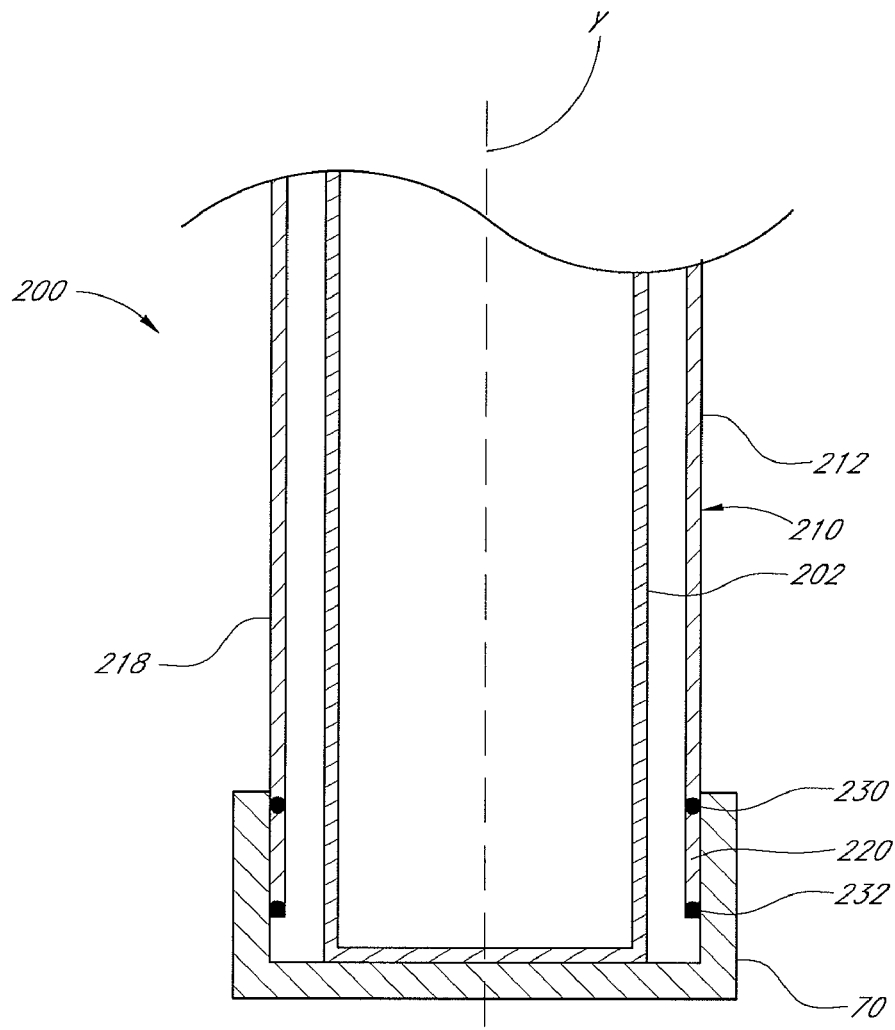
FIG. 17 is a cross-sectional side view of the dressing applicator of FIG. 16 with the spreading portion in an unfolded state.
Figure 18:
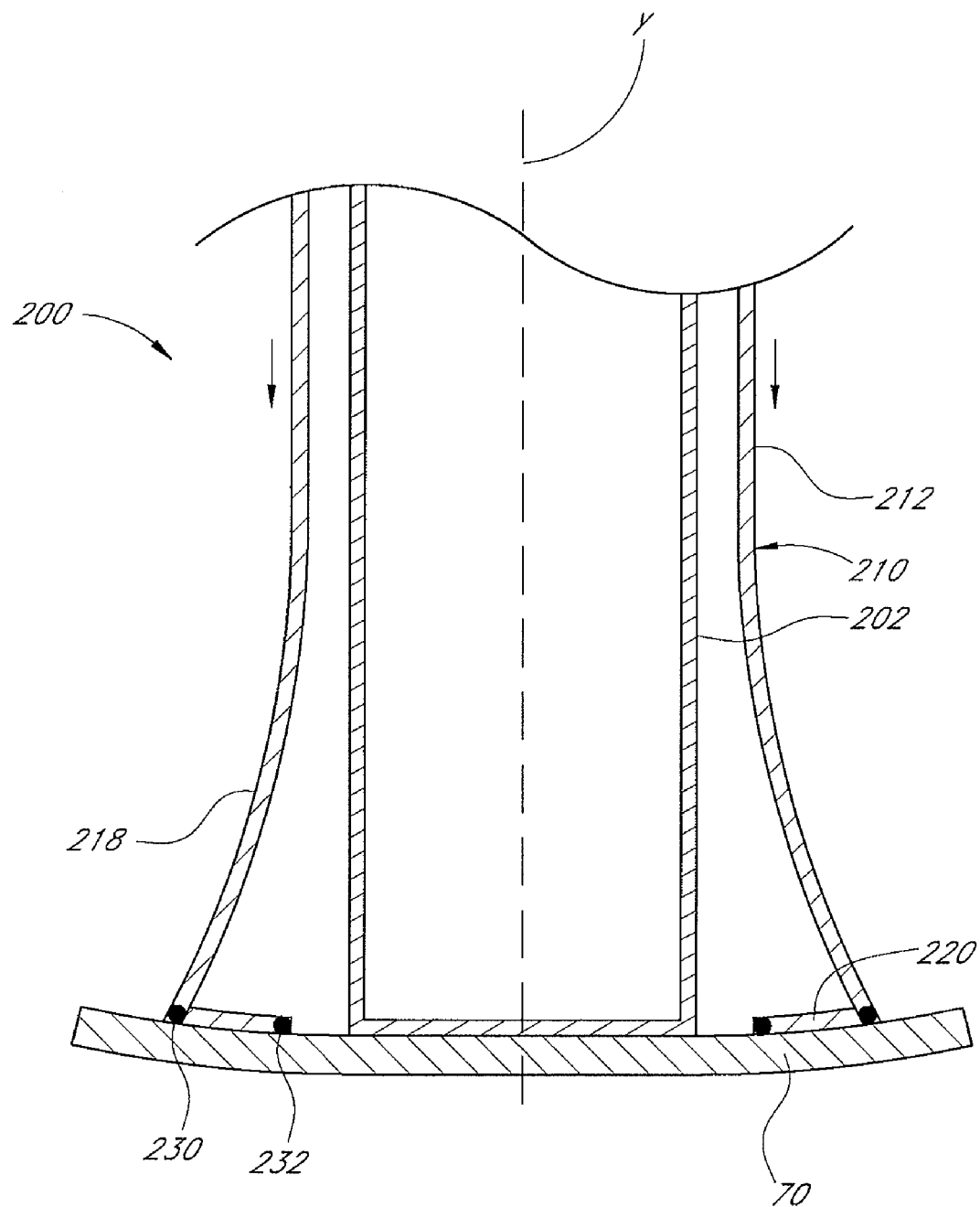
FIG. 18 is a partial perspective view of the dressing applicator of FIG. 16 with the spreading portion in a deployed state.

With reference next to FIGS. 16-18, another embodiment of a dressing applicator 200 comprises a main body 202 and a sleeve 210 that is movable longitudinally relative to the main body 202. The sleeve 210 comprises a generally rigid portion 212 and a spreading portion 214 distal of the rigid portion 212. Preferably the spreading portion 214 is disposed at or adjacent a distal end 216 of the sleeve 210. The spreading portion 214 comprises a plurality of upper segments 218 and a corresponding plurality of lower segments 220. In the illustrated embodiment, the upper segments 218 are coformed with the rigid portion 212, and are defined by side edges 222. Preferably, adjacent upper segments 218 are spaced from each other.

Each lower segment 220 preferably is pivotally attached to a distal end 224 of a respective upper segment 218 at a proximal joint 230. As such, the lower segments 220 are pivotable relative to the upper segments 218 at the proximal joint 230. Each lower segment 220 also is pivotally connected to a distal joint 232 at or adjacent a distal end of the sleeve 210. The lower segment 220 pivots at the distal joint 232. The proximal and distal joints 230, 232 can comprise any structure configured to allow the lower segment 220 to pivot relative to the major axis Y. With particular reference to FIGS. 17 and 18, preferably the lower segments 220 are configured so that each distal joint 232 generally maintains its radial distance from the major axis Y, and the distal joints 232 of successive segments 220 are immediately adjacent on another. Preferably, the distal joints 232 are linked so as not to separate from one another.

With continued reference to FIGS. 16-18, a dressing 70 preferably is disposed about the distal end of the applicator 200. As the dressing 70 engages the wound, the sleeve 210 is pushed distally relative to the main body 202. The generally rigid portion 212 of the sleeve 210 preferably is sufficiently rigid to communicate distal force without substantially buckling. However, as shown in FIG. 18, the upper segments 218 preferably are sufficiently flexible to bend outwardly as the lower segments 220 pivot about the joints 230, 232. As such, when the dressing 70 is deployed, wound engagement pressure is communicated through the upper segments 218 to the lower segments 220 and dressing 70.

In the embodiment illustrated in FIGS. 16-18, a vacuum, light adhesive, or the like may be employed to releasably hold the dressing 70 in place on the applicator 200. Additionally, as with some embodiments disclosed herein, other embodiments may include a locking mechanism. Further, in another embodiment, the upper segments 218 are biased outwardly. Such a bias may be accomplished in any acceptable manner, such as by a ball and detent mechanism as shown and discussed above with reference to FIG. 15. In still further embodiments, a flexible cover may be disposed about the spreading portion to separate the dressing from the applicator and to reduce the likelihood that body tissue or a portion of the dressing may become pinched between segments when the segments are unfolded after deployment.

In practice, the embodiments illustrated in FIGS. 1-18 are advantageously configured to deploy a dressing 70 to an internal wound location W by way of a minimally invasive incision in a patient. Accordingly, the applicator embodiments can be used to close a wound W without requiring the opening of a large incision in the patient's skin. Additionally, the embodiments provide a compact apparatus for applying and spreading a dressing 70 on a wound W. Preferably, the applicator embodiments are configured so that an effective circumference of the applicator expands when deployed to help apply the dressing to the wound and/or surgical field. As discussed above, the segments 78, 80 advantageously provide the applicator embodiments with a means for compressing and/or holding the dressing 70 against the field area F surrounding the wound W, especially when the dressing is considerably larger than the diameter of the applicator.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A dressing delivery system for an internal wound, comprising:
    an elongate sleeve sized for percutaneous insertion in a patient, the sleeve extending about a longitudinal major axis and having a generally rigid portion at a proximal end thereof and at least one foldable portion at a distal end thereof, the foldable portion extending proximally from a distal tip of the sleeve and comprising a preferentially-bending portion that is flexible relative to the proximal rigid portion so as to preferentially bend when the sleeve is exposed to a longitudinal compressive force, the distal tip of the elongate sleeve being unsupported other than by being part of the sleeve;
    a tubular main body extending about a major axis between a proximal end and a distal end, the elongate sleeve being slidably disposed about an outer surface of the tubular main body, and the foldable portion of the elongate sleeve being unconnected to the main body, so that longitudinal relative movement between the body and sleeve does not affect the orientation of the foldable portion of the sleeve; and
    a dressing disposed adjacent to and at least partially distal of the distal end of the sleeve;
    wherein by moving the sleeve into engagement with an internal wound so that the sleeve is subjected to a longitudinal compressive force as the distal end of the sleeve is pressed against the wound, the preferentially-bending portion bends so that the at least one foldable portion pivots about the distal tip so as to move from a first orientation in which the foldable portion is generally parallel to the major axis to a second orientation in which the foldable portion is generally transverse to the major axis so as to urge the dressing against the wound.

2. The dressing delivery system of claim 1, wherein the dressing extends proximally sufficient so that it is disposed about the at least one foldable portion.

3. The dressing delivery system of claim 1, wherein a vacuum aperture is formed through the foldable portion, and in the first orientation the dressing is wrapped about the distal end so as to cover the distal end and extend proximally so as to cover the distal tip of the foldable portion sufficient to cover the vacuum aperture, the sleeve being connected to a source of vacuum, and a vacuum being maintained within a lumen defined by the sleeve so that the dressing is attached to the sleeve via the vacuum when the foldable portion is in the first orientation generally parallel to the major axis.

4. The dressing delivery system of claim 1, wherein the tubular main body further comprises a catch at the main body distal end, the sleeve distal tip and the catch being longitudinally movable relative to one another, the catch configured so that as the sleeve moves distally relative to the main body, the sleeve distal tip engages the catch of the main body.

5. The dressing delivery system of claim 1 further comprising a locking mechanism configured to releasably hold the sleeve in a generally fixed position relative to the tubular main body.

6. The dressing delivery system of claim 1, wherein the dressing comprises a fibrous, non-woven fabric comprising chitosan and a hemostatic agent.

7. The dressing delivery system of claim 6, wherein the hemostatic agent comprises a starch disposed on the fibrous chitosan.

8. The dressing delivery system of claim 1, wherein the elongate sleeve additionally comprises a joint proximal or the distal tip in the preferentially-bending portion, and the foldable portion is defined between the distal tip and the joint, the sleeve adapted to preferentially bend at the joint so that the foldable portion is pivotable about the joint.

9. The dressing delivery system of claim 8 additionally comprising a locking mechanism configured to prevent the foldable portion from pivoting about the joint when in an engaged position and to allow the foldable portion to pivot about the joint when in a disengaged position.

10. The dressing delivery system of claim 9, wherein the locking mechanism comprises an elongate rod that can be selectively advanced adjacent the joint of the sleeve.

11. The dressing delivery system of claim 10, wherein the sleeve additionally comprises a locking member, and the elongate rod extends through the locking member.

12. The dressing delivery system of claim 4, wherein the elongate sleeve additionally comprises a joint proximal of the distal tip, and the foldable portion is defined between the distal tip and the joint, the sleeve adapted to preferentially bend at the joint so that the foldable portion pivots about the joint.

13. The dressing delivery system of claim 3, comprising a plurality of flexible portions disposed adjacent one another, each flexible portion having opposing side edges, wherein in the first orientation the side edges of adjacent flexible portions engage one another so that there is generally no gap between the adjacent portions.

14. The dressing delivery system of claim 13, wherein when in the second orientation the side edges disengage one another so that there are gaps between the side edges of adjacent segments, and vacuum is defeated within the lumen defined by the sleeve.

15. The dressing delivery system of claim 1, wherein the distal end of the sleeve has a diameter, and the diameter remains the same in both the first and second orientations.

16. A method for delivering a dressing to an internal wound, comprising:
  providing an elongate sleeve sized for percutaneous insertion in a patient, the sleeve extending about a longitudinal major axis and having a generally rigid portion at a proximal end thereof and at least one foldable portion at a distal end thereof, the foldable portion extending proximally from a distal tip of the sleeve and comprising a preferentially-bending portion that is flexible relative to the proximal rigid portion so as to preferentially bend when the sleeve is exposed to a longitudinal compressive force, the distal tip of the elongate sleeve being unsupported other than by being part of the sleeve;
  providing a tubular main body extending about a major axis between a proximal end and a distal end, the disposed about an outer surface of the tubular main body, and the foldable portion of the elongate sleeve being unconnected to the main body so that longitudinal relative movement between the body and sleeve does not affect the orientation of the foldable portion of the sleeve;
  providing the sleeve in a first orientation in which the foldable portion is generally parallel to the major axis;
  providing a dressing disposed adjacent to and at least partially distal of the distal end of the sleeve; and
  moving the sleeve into engagement with and pressing against an internal wound so that the sleeve is subjected to a longitudinal compressive force and the preferentially-bending portion bends so that the sleeve buckles outwardly and the at least one foldable portion pivots about the distal tip;
  wherein when the foldable portion pivots about the distal tip the foldable portion moves to a second orientation in which the foldable portion is generally transverse to the major axis; and
  applying a longitudinally directed force to the sleeve so as to urge the dressing against the wound.

17. The method of claim 16, wherein the foldable portion comprises a vacuum aperture formed therethrough, and, providing the sleeve in the first orientation comprises providing the sleeve and dressing with the dressing wrapped about the distal end of the sleeve and foldable portion sufficient to cover the vacuum aperture, and providing a vacuum to a lumen defined within the sleeve, wherein the vacuum is maintained while the sleeve is in the first orientation.

18. The method of claim 17, wherein the sleeve comprises a plurality of foldable portions, each foldable portion having side edges that are positioned adjacent side edges of an adjacent foldable portion when in the first orientation, and wherein when the sleeve moves from the first orientation to the second orientation and the foldable portions pivot, gaps form between the side edges so as to defeat the vacuum.

19. The method of claim 16, wherein providing a dressing comprises providing a dressing so that a portion of the dressing is disposed distal of the distal end of the sleeve and a portion of the dressing is disposed proximal of the distal end of the sleeve, and wherein during the step of applying a longitudinally directed force to the sleeve so as to urge the dressing against the wound, portions of the dressing both distal and proximal of the distal end of the sleeve are urged against the wound.

20. The dressing delivery system of claim 3, wherein the vacuum aperture is disposed proximal of the distal tip of the foldable portion.

21. The dressing delivery system of claim 1, wherein the dressing is detachable from the elongate sleeve.

* * * * *